(12) United States Patent
Dehmlow et al.

(10) Patent No.: US 7,473,705 B2
(45) Date of Patent: Jan. 6, 2009

(54) HEXAFLUOROISOPROPANOL SUBSTITUTED ETHER DERIVATIVES

(75) Inventors: Henrietta Dehmlow, Grenzach-Wyhlen (DE); Bernd Kuhn, Liestal (CH); Narendra Panday, Basel (CH); Hasane Ratni, Habsheim (FR); Matthew Blake Wright, Basel (CH)

(73) Assignee: Hoffmann-LA Roche Inc., Nutley, NJ (US)

( * ) Notice: Subject to any disclaimer, the term of this patent is extended or adjusted under 35 U.S.C. 154(b) by 313 days.

(21) Appl. No.: 11/237,369

(22) Filed: Sep. 28, 2005

(65) Prior Publication Data
US 2006/0074115 A1 Apr. 6, 2006

(30) Foreign Application Priority Data
Oct. 1, 2004 (EP) .................................. 04104818

(51) Int. Cl.
*A61K 31/21* (2006.01)
*C07C 69/76* (2006.01)
(52) U.S. Cl. ..................... 514/506; 514/557; 514/378; 514/383; 548/262.2; 548/240; 560/8; 562/405; 562/262.2
(58) Field of Classification Search .................. 562/405; 548/262.2, 240; 560/8; 514/506, 557, 378, 514/383
See application file for complete search history.

(56) References Cited

U.S. PATENT DOCUMENTS 5,552,437 A * 9/1996 Delorme et al. ............. 514/457

7,319,110 B2 * 1/2008 Lange et al. ................. 514/383

FOREIGN PATENT DOCUMENTS

WO WO 03/099769 12/2003

OTHER PUBLICATIONS

Willy et al., Genes Dev. 1995, 9:1033-45.
Song et al., Proc Natl Acad Sci USA.1994, 91:10809-13.
Miller NE., Lipids 1978, 13:914-9.
Gordon et al., Am J Med. 1977, 62:707-14.
Lund et al., Arterioscler. Thromb. Vasc. Biol. 2003, 23:1169-77.
Joseph and Tontonoz, Curr. Opin. Pharmacol. 2003, 3:192-7.
Cao et al., J Biol Chem. 2003, 278:1131-6.

* cited by examiner

*Primary Examiner*—Rei-tsang Shiao
(74) *Attorney, Agent, or Firm*—George W. Johnston; Dennis P. Tramaloni; Samuel H. Megerditchian

(57) ABSTRACT

The invention is concerned with novel hexafluoroisopropanol substituted ether derivatives of formula (I):

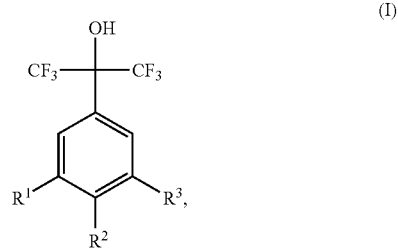

wherein $R^1$ to $R^3$ are as defined in the description and in the claims, as well as physiologically acceptable salts and esters thereof. These compounds bind to LXR alpha and LXR beta and can be used as medicaments.

22 Claims, No Drawings

HEXAFLUOROISOPROPANOL SUBSTITUTED ETHER DERIVATIVES

FIELD OF THE INVENTION

The invention is directed to novel hexafluoroisopropanol substituted ether derivatives of the formula (I):

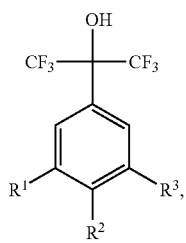

and pharmaceutically acceptable salts and esters thereof.

Further, the invention is directed to a process for the manufacture of the above compounds, pharmaceutical preparations which contain such compounds as well as the use of these compounds for the production of pharmaceutical preparations useful for the treatment of diseases.

All documents cited or relied upon below are expressly incorporated herein by reference.

BACKGROUND OF THE INVENTION

Liver-X-Receptors (LXRs) are members of the nuclear hormone receptor superfamily. The LXRs are activated by endogenous oxysterols and regulate the transcription of genes controlling multiple metabolic pathways. Two subtypes, LXRalpha and LXRbeta, have been described (Willy et al., Genes Dev. 1995, 9:1033-45; Song et al., Proc Natl Acad Sci USA. 1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs are also involved in glucose metabolism, cholesterol metabolism in the brain, cell differentiation, and inflammation.

At present, approximately half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978,13:914-9). The protective function of HDL derives from its role in a process termed reverse cholesterol transport. HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon et al., Am J Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol >240 mg/dl is 37% in diabetic men and 44% in women. The rates for LDL-C >160 mg/dl are 31% and 44%, and for HDL-C <35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund et al., Arterioscler. Thromb. Vasc. Biol. 2003, 23:1169-77). LXRs are also known to control the efflux of cholesterol from the macrophage foam cell of the atherosclerotic lesion, and agonists of LXRs have been shown to be atheroprotective (Joseph and Tontonoz, Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao et al., J Biol Chem. 2003, 278:1131-6). Thus LXR modulators can also show superior therapeutic efficacy on HDL-raising and atheroprotection, with additional effects on diabetes, compared to current therapies.

The novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

Other compounds that bind to and activate LXR alpha and LXR beta have previously been suggested (e.g.: WO 03/099769). However, there is still a need for new compounds with improved properties. The present invention provides the novel compounds of formula (I) which bind to LXR alpha and/or LXR beta. The compounds of the present invention unexpectedly exhibit improved pharmacological properties compared to the compounds known in the art, concerning e.g. metabolic stability, bioavailability and activity.

SUMMARY OF THE INVENTION

In one embodiment of the present invention, provided is a compound according to formula (I):

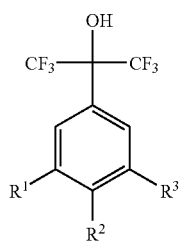

(I)

wherein:

$R^1$ is hydrogen, lower-alkyl, or halogen;

one of $R^2$ and $R^3$ is hydrogen, lower-alkyl, or halogen; and the other of $R^2$ and $R^3$ is —O—CHR$^4$—(CH$_2$)$_m$—(CHR$^5$)$_n$—R$^6$;

$R^4$ is hydrogen, lower-alkyl, aryl, aryl-lower-alkyl, heteroaryl, or heteroaryl-lower-alkyl;

$R^5$ is hydrogen or aryl;

$R^6$ is phenyl or aryl-lower-alkyl, which phenyl or aryl-lower-alkyl is optionally substituted with 1 to 3 substituents selected from the group consisting of amino, halogen, lower-alkyl, fluoro-lower-alkyl, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy and aryl-lower-alkoxy;

or $R^6$ is 5- to 6-membered monocyclic heteroaryl which is optionally substituted with 1 to 3 substituents selected from the group consisting of lower-alkyl, fluoro-lower-alkyl, halogen and aryl, which aryl is optionally substituted with 1 to 3 substituents selected from the group consisting of amino, halogen, lower-alkyl, fluoro-lower-alkyl, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy and aryl-lower-alkoxy;

or $R^6$ is 9-membered bicyclic heteroaryl which is optionally substituted with 1 to 3 substituents selected from the group consisting of lower-alkyl, fluoro-lower-alkyl, halogen and aryl, which aryl is optionally substituted with 1 to 3 substituents selected from the group consisting of, amino, halogen, lower-alkyl, fluoro-lower-alkyl, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy and aryl-lower-alkoxy;

or $R^6$ is heteroaryl-lower-alkyl which is optionally substituted with 1 to 3 substituents selected from the group consisting of lower-alkyl, fluoro-lower-alkyl, halogen and aryl, which aryl is optionally substituted with 1 to 3 substituents selected from the group consisting of amino, halogen, lower-alkyl, fluoro-lower-alkyl, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy and aryl-lower-alkoxy;

or $R^6$ is —O—$R^7$ or lower-alkyl-O$R^7$;

$R^7$ is aryl which is optionally substituted with 1 to 3 substituents selected from the group consisting of amino, halogen, lower-alkyl, fluoro-lower-alkyl, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy and aryl-lower-alkoxy;

or $R^7$ is heteroaryl which is optionally substituted with 1 to 3 substituents selected from the group consisting of lower-alkyl, fluoro-lower-alkyl, halogen, amino, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy, aryl-lower-alkoxy and aryl, which aryl is optionally substituted with 1 to 3 substituents selected from the group consisting of lower-alkyl and halogen;

$R^8$, $R^9$, $R^{10}$, $R^{11}$, $R^{12}$ and $R^{13}$ independently from each other are hydrogen or lower-alkyl;

m is 0 to 3;

n is 0 or 1;

and pharmaceutically acceptable salts and esters thereof.

In another embodiment of the present invention, provided is a process for the manufacture of a compound, or a pharmaceutically acceptable salt or ester, according to formula I, comprising the steps of:

reacting a compound of formula (II)

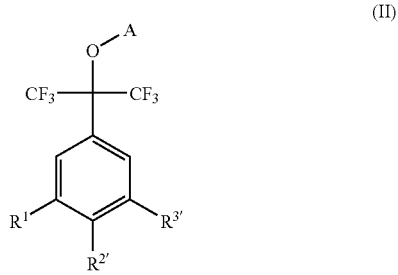

(II)

with a compound HO—CHR$^4$—(CH$_2$)$_m$—(CHR$^5$)$_n$—R$^6$, wherein $R^1$, $R^4$, $R^5$, $R^6$, m and n are as defined in any of claims 1-20, one of $R^{2'}$ and $R^{3'}$ is OH and the other of $R^{2'}$ and $R^{3'}$ is hydrogen, lower-alkyl, or halogen, and A is hydrogen or a protecting group, or reacting a compound of formula (II)

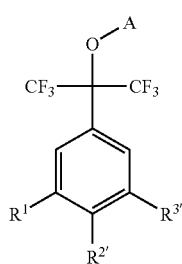

(II)

with a compound LG-CHR$^4$—(CH$_2$)$_m$—(CHR$^5$)$_n$—R$^6$ wherein R$^1$, R$^4$, R$^5$, R$^6$, m and n are as defined in any of claims 1-20, one of R$^{2'}$ and R$^{3'}$ is OH and the other of R$^{2'}$ and R$^{3'}$ is hydrogen, lower-alkyl, or halogen, LG is a leaving group and A is hydrogen or a protecting group.

In a further embodiment of the present invention, provided is a pharmaceutical composition comprising a therapeutically effective amount of a compound according to formula I, or a pharmaceutically acceptable salt or ester thereof, and a pharmaceutically acceptable carrier and/or adjuvant.

In a still further embodiment of the present invention, provided is a method for the therapeutic and/or prophylactic treatment of diseases which are modulated by LXR alpha and/or LXR beta agonists, comprising the step of administering a therapeutically effective amount of a compound according to formula I, or a pharmaceutically acceptable salt or ester thereof, to a human being or animal in need thereof.

DETAILED DESCRIPTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted, e.g. by hydroxy. Such substituted lower-alkyl-groups are referred to as "hydroxy-lower-alkyl". Unsubstituted lower-alkyl groups are preferred The term "fluoro-lower-alkyl" refers to lower-alkyl groups which are mono- or multiply substituted with fluorine. Examples of fluoro-lower-alkyl groups are e.g. CFH$_2$, CF$_2$H, CF$_3$, CF$_3$CH$_2$, CF$_3$(CH$_2$)$_2$, (CF$_3$)$_2$CH and CF$_2$H-CF$_2$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl.

Examples of fluoro-lower-alkoxy groups are e.g. CFH$_2$—O, CF$_2$H—O, CF$_3$—O, CF$_3$CH$_2$—O, CF$_3$(CH$_2$)$_2$—O, (CF$_3$)$_2$CH—O, and CF$_2$H—CF$_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, halogen, hydroxy, CN, CF$_3$, amino, aminocarbonyl, carboxy, NO$_2$, dioxo-lower-alkylene (forming e.g. a benzodioxyl group), lower-alkylsufonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, cycloalkyl, phenyloxy and methyl-oxadiazolyl. Preferred substituents are halogen, lower-alkyl, fluoro-lower-alkyl and CN. Furthermore, aryl groups can be substituted as described in the description below.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl and benzoisoxazolyl. Preferred heteroaryl groups are pyridinyl, pyrimidinyl, isoxazolyl, oxazolyl and triazolyl. A heteroaryl group may have a substitution pattern as described earlier in connection with the term "aryl". A heteroaryl may further be substituted as described in the description below.

The term "5 to 6 membered monocyclic heteroaryl" refers to an aromatic 5 to 6 membered monocyclic ring as described above in context with the term "heteroaryl", which can be substituted as described above or as described below in the description. Examples of 5 to 6 membered monocyclic heteroaryl groups are furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl and 1,2,3-thiadiazolyl. Preferred are oxazolyl, isoxazolyl and triazolyl. A 5 to 6 membered monocyclic heteroaryl group may have a substitution pattern e.g. as described earlier in connection with the term "aryl". Preferably, a heteroaryl may further be substituted as described in the description below.

The term "9 membered bicyclic heteroaryl" refers to an aromatic 9 membered bicyclic ring which can comprise 1, 2 or 3 atoms selected from nitrogen, oxygen and/or sulphur, as described above in context with the term "heteroaryl", which can be substituted as described above or as described below in the description. Examples of 9 membered bicyclic heteroaryl groups are benzoimidazolyl, indolyl, indazolyl, benzoisothiazolyl, benzoxazolyl and benzoisoxazolyl. Preferred 9 membered bicyclic heteroaryl groups are benzoisothiazolyl and benzoisoxazolyl. A 9 membered bicyclic heteroaryl group may have a substitution pattern e.g. as described earlier in connection with the term "aryl". Preferably, a heteroaryl may further be substituted as described in the description below.

The term "leaving group" refers to a group that may be displaced by a nucleophile (e.g. a secondary amine). Typical leaving groups are e.g.: Cl, Br, I, O—SO$_2$-lower-alkyl (wherein O—SO$_2$—CH$_3$=OMs), O—SO$_2$-lower-fluoroalkyl (wherein O—SO$_2$—CF$_3$=OTf), O—SO$_2$-aryl (wherein wherein O—SO$_2$-ptolyl=OTs), O-(para-nitrophenyl).

The term "protecting group" refers to groups which are used to protect functional groups, particularly hydroxy groups, temporarily. Examples of protecting groups are benzyl, p-methoxybenzyl, t-butyl-dimethylsilyl and t-butyl-diphenylsilyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

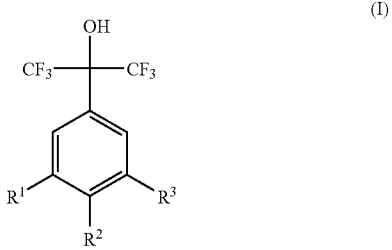

wherein
R$^1$ is hydrogen, lower-alkyl, or halogen;
one of R$^2$ and R$^3$ is hydrogen, lower-alkyl, or halogen; and the other of R$^2$ and R$^3$ is —O—CHR$^4$—(CH$_2$)$_m$—(CHR$^5$)$_n$—R$^6$;
R$^4$ is hydrogen, lower-alkyl, aryl, aryl-lower-alkyl, heteroaryl, or heteroaryl-lower-alkyl;
R$^5$ is hydrogen or aryl;
R$^6$ is phenyl or aryl-lower-alkyl, which phenyl or aryl-lower-alkyl is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is 5- to 6-membered monocyclic heteroaryl which is optionally substituted with 1 to 3 substituents selected from the group consisting of lower-alkyl, fluoro-lower-alkyl, halogen and aryl, which aryl is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is 9-membered bicyclic heteroaryl which is optionally substituted with 1 to 3 substituents selected from the group consisting of lower-alkyl, fluoro-lower-alkyl, halogen and aryl, which aryl is optionally substituted with 1 to 3 substituents selected from the group consisting of, amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is heteroaryl-lower-alkyl which is optionally substituted with 1 to 3 substituents selected from the group consisting of lower-alkyl, fluoro-lower-alkyl, halogen and aryl, which aryl is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is —O—R$^7$ or lower-alkyl-OR$^7$;
R$^7$ is aryl which is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^7$ is heteroaryl which is optionally substituted with 1 to 3 substituents selected from the group consisting of lower-alkyl, fluoro-lower-alkyl, halogen, amino, hydroxy-lower-alkyl, $R^8$—O—C(O)—, $R^9R^{10}$NC(O)—, $R^{11}$—O—C(O)-lower-alkyl, $R^{12}R^{13}$NC(O)-lower-alkyl, lower-alkoxy, aryl-lower-alkoxy and aryl, which aryl is optionally substituted with 1 to 3 substituents selected from the group consisting of lower-alkyl and halogen;

$R^8$, $R^9$, $R^{10}$, $R^{11}$, $R^{12}$ and $R^{13}$ independently from each other are hydrogen or lower-alkyl;

m is 0 to 3;

n is 0 or 1;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

Preferred compounds of formula (I) as described above are those, wherein $R^1$ is hydrogen, chlorine or methyl. Hydrogen, chlorine and methyl individually constitute preferred embodiments.

Other preferred compounds of formula (I) as described above are those, wherein one of $R^2$ and $R^3$ is hydrogen or lower-alkyl, and the other of $R^2$ and $R^3$ is —O—CHR$^4$—(CH$_2$)$_m$—(CHR$^5$)$_n$—R$^6$, wherein $R^4$, $R^5$, $R^6$, m and n are as defined above. More preferred are those compounds, wherein $R^2$ is —O—CHR$^4$—(CH$_2$)$_m$—(CHR$^5$)$_n$—R$^6$, and $R^3$ is hydrogen, wherein $R^4$, $R^5$, $R^6$, m and n are as defined above.

Another preferred embodiment of the present invention relates to compounds of formula (I) as described above, wherein $R^4$ is hydrogen, lower-alkyl, aryl, or aryl-lower-alkyl, more preferably wherein $R^4$ is hydrogen, lower-alkyl, or aryl-lower-alkyl, most preferably wherein $R^4$ is hydrogen, methyl or benzyl. Hydrogen, methyl and benzyl individually constitute preferred embodiments.

Other preferred compounds of formula (I) as described above are those, wherein n is 1 and $R^5$ is aryl, especially wherein n is 1 and $R^5$ is phenyl.

Compounds wherein $R^6$ is phenyl which is optionally substituted with $R^8$—O—C(O)—, or $R^6$ is 5- to 6-membered monocyclic heteroaryl which is optionally substituted with 1 to 3 substituents selected from the group consisting of lower-alkyl and aryl, which aryl is optionally substituted with 1 to 3 substituents selected from the group consisting of halogen, lower-alkyl, fluoro-lower-alkyl, hydroxy-lower-alkyl, $R^8$—O—C(O)— and $R^9R^{10}$NC(O)—, wherein $R^8$, $R^9$ and $R^{10}$ are as defined above, are also preferred. Particularly preferred are those compounds wherein $R^6$ is phenyl, or $R^6$ is oxazolyl, which oxazolyl is substituted with lower-alkyl and phenyl, which phenyl is substituted with halogen, fluoro-lower-alkyl or hydroxy-lower-alkyl. More particularly preferred are those compounds wherein $R^6$ is phenyl, 2-(3-chloro-phenyl)-5-methyl-oxazol-4-yl, 5-methyl-2-(3-trifluoromethyl-phenyl)-oxazol-4-yl, or 2-(3-hydroxymethyl-phenyl)-5-methyl-oxazol-4-yl.

Another preferred embodiment of the present invention relates to compounds of formula (I) as described above, wherein $R^6$ is —O—$R^7$, wherein $R^7$ is phenyl which is substituted with 1 substituent selected from the group consisting of hydroxy-lower-alkyl, $R^{11}$—O—C(O)-lower-alkyl and $R^{12}R^{13}$NC(O)-lower-alkyl, or $R^7$ is heteroaryl selected from the group consisting of benzo[d]isothiazolyl and benzo[d]isoxazolyl, which heteroaryl is optionally substituted with 1 to 2 substituents selected from the group consisting of lower-alkyl, fluoro-lower-alkyl and phenyl, which phenyl is optionally substituted with halogen, wherein $R^{11}$, $R^{12}$ and $R^{13}$ are as defined above. Preferably, $R^7$ is phenyl substituted with lower-alkoxy-carbonyl or lower-alkoxy-carbonyl-lower-alkyl. More preferably, $R^7$ is 3-methoxycarbonylmethyl-phenyl, 4-methoxycarbonylmethyl-phenyl, or 4-methoxycarbonyl-phenyl.

Another preferred embodiment of the present invention relates to compounds as defined above, wherein m is 0 to 2, particularly wherein m is 0 or 1. Compounds wherein m is 0 and wherein m is 1 individually constitute preferred embodiments of the present invention. Other preferred compounds are those, wherein n is 0.

In a preferred embodiment of the present invention, m is 0 to 2, more preferably m is 0 or 1. Compounds of formula (I) as described above, wherein n is 0 also constitute a preferred embodiment of the present invention.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:

2-(4-{3-[3-(4-Bromo-phenyl)-benzo[d]isothiazol-6-yloxy]-propoxy}-phenyl)-1,1,1,3,3,3-hexafluoro-propan-2-ol, 3-(3-{3-[3-(2,2,2-Trifluoro-1-hydroxy-1-trifluoromethyl-ethyl)-phenoxy]-propoxy}-phenyl)-propionic acid ethyl ester, rac (4-{1-Phenyl-2-[3-(2,2,2-trifluoro-1-hydroxy-1-trifluoromethyl-ethyl)-phenoxy]-ethoxy}-phenyl)-acetic acid methyl ester, rac (4-{1-Phenyl-2-[3-(2,2,2-trifluoro-1-hydroxy-1-trifluoromethyl-ethyl)-phenoxy]-ethoxy}-phenyl)-acetic acid, rac 4-{1-Phenyl-2-[4-(2,2,2-trifluoro-1-hydroxy-1-trifluoromethyl-ethyl) -phenoxy]-ethoxy}-benzoic acid methyl ester, 4-{2-[4-(2,2,2-Trifluoro-1-hydroxy-1-trifluoromethyl-ethyl)-phenoxy]-ethoxy}-benzoic acid methyl ester, 2-(4-Benzyloxy-3-chloro-phenyl)-1,1,1,3,3,3-hexafluoro-propan-2-ol, 2-(4-Benzyloxy-3-methyl-phenyl) -1,1,1,3,3,3-hexafluoro-propan-2-ol, 2-(3-Benzyloxy-phenyl)-1,1,1,3,3,3-hexafluoro-propan-2-ol, 2-(4-Benzyloxy-3,5-dimethyl-phenyl)-1,1,1,3,3,3-hexafluoro-propan-2-ol, 2-(4-Benzyloxy-phenyl)-1,1,1,3,3,3-hexafluoro-propan-2-ol, (4-{3-[2-Methyl-4-(2,2,2-trifluoro-1-hydroxy-1-trifluoromethyl-ethyl)-phenoxy]-propoxy}-phenyl)-acetic acid methyl ester, 4-{3-[2-Methyl-4-(2,2,2-trifluoro-1-hydroxy-1-trifluoromethyl-ethyl)-phenoxy]-propoxy}-benzoic acid methyl ester, 3-(4-{3-[2-Chloro-4-(2,2,2-trifluoro-1-hydroxy-1-trifluoromethyl-ethyl)-phenoxy]-propoxy}-phenyl)-propionic acid methyl ester, (4-{3-[2-Chloro-4-(2,2,2-trifluoro-1-hydroxy-1-trifluoromethyl-ethyl)-phenoxy]-propoxy}-phenyl)-acetic acid methyl ester, 4-{3-[2-Chloro-4-(2,2,2-trifluoro-1-hydroxy-1-trifluoromethyl-ethyl)-phenoxy]-propoxy}-benzoic acid methyl ester, (4-{3-[2,6-Dimethyl-4-(2,2,2-trifluoro-1-hydroxy-1-trifluoromethyl-ethyl)-phenoxy]-propoxy}-phenyl)-acetic acid methyl ester, 4-{3-[2,6-Dimethyl-4-(2,2,2-trifluoro-1-hydroxy-1-trifluoromethyl-ethyl)-phenoxy]-propoxy}-benzoic acid methyl ester,
4-{3-[2-Methyl-4-(2,2,2-trifluoro-1-hydroxy-1-trifluoromethyl-ethyl)-phenoxy]-propoxy}-benzoic acid,
(4-{3-[2-Methyl-4-(2,2,2-trifluoro-1-hydroxy-1-trifluoromethyl-ethyl)-phenoxy]-propoxy}-phenyl)-acetic acid,
(4-{3-[2,6-Dimethyl-4-(2,2,2-trifluoro-1-hydroxy-1-trifluoromethyl-ethyl)-phenoxy]-propoxy}-phenyl)-acetic acid,
4-{3-[2,6-Dimethyl-4-(2,2,2-trifluoro-1-hydroxy-1-trifluoromethyl-ethyl)-phenoxy]-propoxy}-benzoic acid,
4-{2-[2,6-Dimethyl-4-(2,2,2-trifluoro-1-hydroxy-1-trifluoromethyl-ethyl)-phenoxy]-ethoxy}-benzoic acid methyl ester,
3-(4-{(S)-2-[2-Methyl-4-(2,2,2-trifluoro-1-hydroxy-1-trifluoromethyl-ethyl)-phenoxy]-3-phenyl-propoxy}-phenyl)-propionic acid methyl ester,
(4-{(S)-2-[2-Methyl-4-(2,2,2-trifluoro-1-hydroxy-1-trifluoromethyl-ethyl)-phenoxy]-3-phenyl-propoxy}-phenyl)-acetic acid methyl ester,
4-{(S)-2-[2-Methyl-4-(2,2,2-trifluoro-1-hydroxy-1-trifluoromethyl-ethyl)-phenoxy]-3-phenyl-propoxy}-benzoic acid methyl ester,
(4-{(S)-3-Phenyl-2-[4-(2,2,2-trifluoro-1-hydroxy-1-trifluoromethyl-ethyl)-phenoxy]-propoxy}-phenyl)-acetic acid methyl ester,
4-{(S)-3-Phenyl-2-[4-(2,2,2-trifluoro-1-hydroxy-1-trifluoromethyl-ethyl)-phenoxy]-propoxy}-benzoic acid methyl ester,
(4-{(S)-2-[2-Methyl-4-(2,2,2-trifluoro-1-hydroxy-1-trifluoromethyl-ethyl)-phenoxy]-3-phenyl-propoxy}-phenyl)-acetic acid,
4-{(S)-2-[2-Methyl-4-(2,2,2-trifluoro-1-hydroxy-1-trifluoromethyl-ethyl)-phenoxy]-3-phenyl-propoxy}-benzoic acid,
(4-{(S)-3-Phenyl-2-[4-(2,2,2-trifluoro-1-hydroxy-1-trifluoromethyl-ethyl)-phenoxy]-propoxy}-phenyl)-acetic acid,
4-{(S)-3-Phenyl-2-[4-(2,2,2-trifluoro-1-hydroxy-1-trifluoromethyl-ethyl)-phenoxy]-propoxy}-benzoic acid,
rac 1,1,1,3,3,3-Hexafluoro-2-{4-[2-(4-hydroxymethyl-phenoxy)-1-phenyl-ethoxy]-phenyl}-propan-2-ol,
1,1,1,3,3,3-Hexafluoro-2-(3-methyl-4-phenethyloxy-phenyl)-propan-2-ol,
rac 1,1,1,3,3,3-Hexafluoro-2-[3-methyl-4-(1-phenyl-ethoxy)-phenyl]-propan-2-ol,
2-{4-[2-(3-Chloro-phenyl)-5-methyl-oxazol-4-ylmethoxy]-phenyl}-1,1,1,3,3,3-hexafluoro-propan-2-ol,
2-[4-(3,5-Dimethyl-isoxazol-4-ylmethoxy)-phenyl]-1,1,1,3,3,3-hexafluoro-propan-2-ol,
1,1,1,3,3,3-Hexafluoro-2-[4-(5-methyl-isoxazol-3-ylmethoxy)-phenyl]-propan-2-ol,
1,1,1,3,3,3-Hexafluoro-2-[4-(5-methyl-2-phenyl-2H-[1,2,3]triazol-4-ylmethoxy)-phenyl]-propan-2-ol,
1,1,1,3,3,3-Hexafluoro-2-[4-(5-methyl-3-phenyl-isoxazol-4-ylmethoxy)-phenyl]-propan-2-ol,
3-[4-(2,2,2-Trifluoro-1-hydroxy-1-trifluoromethyl-ethyl)-phenoxymethyl]-benzoic acid methyl ester,
4-{(S)-2-[2-methyl-4-(2,2,2-trifluoro-1-hydroxy-1-trifluoromethyl-ethyl)-phenoxy]-3-phenyl-propoxy}-benzoic acid,
(4-{(S)-3-phenyl-2-[4-(2,2,2-trifluoro-1-hydroxy-1-trifluoromethyl-ethyl)-phenoxy]-propoxy}-phenyl)-acetic acid,
3-(4-{(R)-3-Phenyl-2-[4-(2,2,2-trifluoro-1-hydroxy-1-trifluoromethyl-ethyl)-phenoxy]-propoxy}-phenyl)-propionic acid methyl ester,
(4-{(R)-3-Phenyl-2-[4-(2,2,2-trifluoro-1-hydroxy-1-trifluoromethyl-ethyl)-phenoxy]-propoxy}-phenyl)-acetic acid methyl ester,
4-{(R)-3-Phenyl-2-[4-(2,2,2-trifluoro-1-hydroxy-1-trifluoromethyl-ethyl)-phenoxy]-propoxy}-benzoic acid methyl ester,
3-(4-{(R)-3-Phenyl-2-[4-(2,2,2-trifluoro-1-hydroxy-1-trifluoromethyl-ethyl)-phenoxy]-propoxy}-phenyl)-propionic acid,
(4-{(R)-3-Phenyl-2-[4-(2,2,2-trifluoro-1-hydroxy-1-trifluoromethyl-ethyl)-phenoxy]-propoxy}-phenyl)-acetic acid,
4-{(R)-3-Phenyl-2-[4-(2,2,2-trifluoro-1-hydroxy-1-trifluoromethyl-ethyl)-phenoxy]-propoxy}-benzoic acid,
2-{4-[2-(3-Chloro-phenyl)-5-methyl-oxazol-4-ylmethoxy]-3-methyl-phenyl}-1,1,1,3,3,3-hexafluoro-propan-2-ol,
2-{3-Chloro-4-[2-(3-chloro-phenyl)-5-methyl-oxazol-4-ylmethoxy]-phenyl}-1,1,1,3,3,3-hexafluoro-propan-2-ol,
1,1,1,3,3,3-Hexafluoro-2-(4-phenethyloxy-phenyl)-propan-2-ol,
2-(3,5-Dimethyl-4-phenethyloxy-phenyl)-1,1,1,3,3,3-hexafluoro-propan-2-ol,
2-(3-Chloro-4-phenethyloxy-phenyl)-1,1,1,3,3,3-hexafluoro-propan-2-ol,
rac 1,1,1,3,3,3-Hexafluoro-2-[4-(1-phenyl-ethoxy)-phenyl]-propan-2-ol,
1,1,1,3,3,3-Hexafluoro-2-[3-methyl-4-(5-methyl-2-m-tolyl-oxazol-4-ylmethoxy)-phenyl]-propan-2-ol,
2-{4-[2-(2-Chloro-phenyl)-5-methyl-oxazol-4-ylmethoxy]-3-methyl-phenyl}-1,1,1,3,3,3-hexafluoro-propan-2-ol,
1,1,1,3,3,3-Hexafluoro-2-[3-methyl-4-(5-methyl-2-o-tolyl-oxazol-4-ylmethoxy)-phenyl]-propan-2-ol,
1,1,1,3,3,3-Hexafluoro-2-{3-methyl-4-[5-methyl-2-(3-trifluoromethyl-phenyl)-oxazol-4-ylmethoxy]-phenyl}-propan-2-ol,
1,1,1,3,3,3-Hexafluoro-2-{4-[2-(4-fluoro-3-methyl-phenyl)-5-methyl-oxazol-4-ylmethoxy]-3-methyl-phenyl}-propan-2-ol,
2-{3-Chloro-4-[5-methyl-2-(4-trifluoromethyl-phenyl)-oxazol-4-ylmethoxy]-phenyl}-1,1,1,3,3,3-hexafluoro-propan-2-ol,
2-[3-Chloro-4-(5-methyl-2-m-tolyl-oxazol-4-ylmethoxy)-phenyl]-1,1,1,3,3,3-hexafluoro-propan-2-ol,
2-{3-Chloro-4-[2-(2-chloro-phenyl)-5-methyl-oxazol-4-ylmethoxy]-phenyl}-1,1,1,3,3,3-hexafluoro-propan-2-ol,
2-[3-Chloro-4-(5-methyl-2-o-tolyl-oxazol-4-ylmethoxy)-phenyl]-1,1,1,3,3,3-hexafluoro-propan-2-ol,
2-{3-Chloro-4-[5-methyl-2-(3-trifluoromethyl-phenyl)-oxazol-4-ylmethoxy]-phenyl}-1,1,1,3,3,3-hexafluoro-propan-2-ol,
2-{3-Chloro-4-[2-(4-fluoro-3-methyl-phenyl)-5-methyl-oxazol-4-ylmethoxy]-phenyl}-1,1,1,3,3,3-hexafluoro-propan-2-ol,
2-{3-[2-(3-Chloro-phenyl)-5-methyl-oxazol-4-ylmethoxy]-phenyl}-1,1,1,3,3,3-hexafluoro-propan-2-ol,
1,1,1,3,3,3-Hexafluoro-2-[3-(5-methyl-2-o-tolyl-oxazol-4-ylmethoxy)-phenyl]-propan-2-ol,
1,1,1,3,3,3-Hexafluoro-2-{3-[5-methyl-2-(3-trifluoromethyl-phenyl)-oxazol-4-ylmethoxy]-phenyl}-propan-2-ol,
2-{3-[2-(2-Chloro-phenyl)-5-methyl-oxazol-4-ylmethoxy]-phenyl}-1,1,1,3,3,3-hexafluoro-propan-2-ol,
1,1,1,3,3,3-Hexafluoro-2-[3-(5-methyl-2-m-tolyl-oxazol-4-ylmethoxy)-phenyl]-propan-2-ol,
3-{4-[2-Chloro-4-(2,2,2-trifluoro-1-hydroxy-1-trifluoromethyl-ethyl)-phenoxymethyl]-5-methyl-oxazol-2-yl}-benzoic acid methyl ester, 2-{3-Chloro-4-[2-(3-hydroxymethyl-phenyl)-5-methyl-oxazol-4-ylmethoxy]-phenyl}-1,1,1,3,3,3-hexafluoro-propan-2-ol,
4-{5-Methyl-4-[3-(2,2,2-trifluoro-1-hydroxy-1-trifluoromethyl-ethyl)-phenoxymethyl]-oxazol-2-yl}-benzoic acid methyl ester,
4-{5-Methyl-4-[3-(2,2,2-trifluoro-1-hydroxy-1-trifluoromethyl-ethyl)-phenoxymethyl]-oxazol-2-yl}-benzoic acid,
N,N-Dimethyl-4-{5-methyl-4-[3-(2,2,2-trifluoro-1-hydroxy-1-trifluoromethyl-ethyl)-phenoxymethyl]-oxazol-2-yl}-benzamide,
(3-{2-[4-(2,2,2-Trifluoro-1-hydroxy-1-trifluoromethyl-ethyl)-phenoxy]-ethoxy}-phenyl)-acetic acid methyl ester,
(4-{2-[4-(2,2,2-Trifluoro-1-hydroxy-1-trifluoromethyl-ethyl)-phenoxy]-ethoxy}-phenyl)-acetic acid methyl ester,
(3-{2-[3-(2,2,2-Trifluoro-1-hydroxy-1-trifluoromethyl-ethyl)-phenoxy]-ethoxy}-phenyl)-acetic acid methyl ester,
(3-{2-[4-(2,2,2-Trifluoro-1-hydroxy-1-trifluoromethyl-ethyl)-phenoxy]-ethoxy}-phenyl)-acetic acid,
(4-{2-[4-(2,2,2-Trifluoro-1-hydroxy-1-trifluoromethyl-ethyl)-phenoxy]-ethoxy}-phenyl)-acetic acid,
rac (3-{1-Phenyl-2-[3-(2,2,2-trifluoro-1-hydroxy-1-trifluoromethyl-ethyl)-phenoxy]-ethoxy}-phenyl)-acetic acid methyl ester,
rac (3-{1-Phenyl-2-[3-(2,2,2-trifluoro-1-hydroxy-1-trifluoromethyl-ethyl)-phenoxy]-ethoxy}-phenyl)-acetic acid,
rac N,N-Dimethyl-2-(3-{1-phenyl-2-[3-(2,2,2-trifluoro-1-hydroxy-1-trifluoromethyl-ethyl)-phenoxy]-ethoxy}-phenyl)-acetamide,
2-(4-{2-[3-(4-Bromo-phenyl)-benzo[d]isothiazol-6-yloxy]-ethoxy}-phenyl)-1,1,1,3,3,3-hexafluoro-propan-2-ol,
1,1,1,3,3,3-Hexafluoro-2-{4-[3-(7-propyl-3-trifluoromethyl-benzo[d] isoxazol-6-yloxy)-propoxy]-phenyl}-propan-2-ol,
1,1,1,3,3,3-Hexafluoro-2-{3-[3-(7-propyl-3-trifluoromethyl-benzo [d]isoxazol-6-yloxy)-propoxy]-phenyl}-propan-2-ol,
(4-{3-[3-(2,2,2-Trifluoro-1-hydroxy-1-trifluoromethyl-ethyl)-phenoxy]-propoxy}-phenyl)-acetic acid methyl ester,
(3-{3-[3-(2,2,2-Trifluoro-1-hydroxy-1-trifluoromethyl-ethyl)-phenoxy]-propoxy}-phenyl)-acetic acid methyl ester,
3-(4-{3-[3-(2,2,2-Trifluoro-1-hydroxy-1-trifluoromethyl-ethyl)-phenoxy]-propoxy}-phenyl)-propionic acid methyl ester, and
3-(4-{3-[3-(2,2,2-Trifluoro-1-hydroxy-1-trifluoromethyl-ethyl)-phenoxy]-propoxy}-phenyl)-propionic acid,
and pharmaceutically acceptable salts and esters thereof.

Particularly preferred compounds of formula (I) are those selected from the group consisting of
(3-{2-[4-(2,2,2-Trifluoro-1-hydroxy-1-trifluoromethyl-ethyl)-phenoxy]-ethoxy}-phenyl)-acetic acid methyl ester,
rac 4-{1-Phenyl-2-[4-(2,2,2-trifluoro-1-hydroxy-1-trifluoromethyl-ethyl)-phenoxy]-ethoxy}-benzoic acid methyl ester,
2-(4-Benzyloxy-3-chloro-phenyl)-1,1,1,3,3,3-hexafluoro-propan-2-ol,
(4-{(S)-3-Phenyl-2-[4-(2,2,2-trifluoro-1-hydroxy-1-trifluoromethyl-ethyl)-phenoxy]-propoxy}-phenyl)-acetic acid methyl ester,
1,1,1,3,3,3-Hexafluoro-2-(3-methyl-4-phenethyloxy-phenyl)-propan-2-ol,
rac 1,1,1,3,3,3-Hexafluoro-2-[3-methyl-4-(1-phenyl-ethoxy)-phenyl]-propan-2-ol,
2-{4-[2-(3-Chloro-phenyl)-5-methyl-oxazol-4-ylmethoxy]-phenyl}-1,1,1,3,3,3-hexafluoro-propan-2-ol,
(4-{(R)-3-Phenyl-2-[4-(2,2,2-trifluoro-1-hydroxy-1-trifluoromethyl-ethyl)-phenoxy]-propoxy}-phenyl)-acetic acid methyl ester,
2-{3-Chloro-4-[2-(3-chloro-phenyl)-5-methyl-oxazol-4-ylmethoxy]-phenyl}-1,1,1,3,3,3-hexafluoro-propan-2-ol,
2-(3-Chloro-4-phenethyloxy-phenyl)-1,1,1,3,3,3-hexafluoro-propan-2-ol,
1,1,1,3,3,3-Hexafluoro-2-{3-methyl-4-[5-methyl-2-(3-trifluoromethyl-phenyl)-oxazol-4-ylmethoxy]-phenyl}-propan-2-ol,
2-{3-Chloro-4-[5-methyl-2-(3-trifluoromethyl-phenyl)-oxazol-4-ylmethoxy]-phenyl}-1,1,1,3,3,3-hexafluoro-propan-2-ol, and
2-{3-Chloro-4-[2-(3-hydroxymethyl-phenyl)-5-methyl-oxazol-4-ylmethoxy]-phenyl}-1,1,1,3,3,3-hexafluoro-propan-2-ol,
and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises
reacting a compound of formula (II)

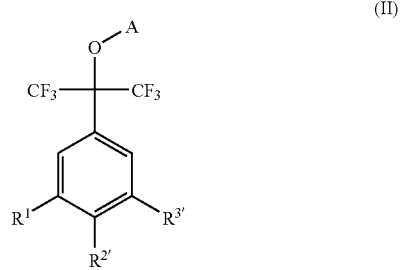

with a compound HO—CHR$^4$—(CH$_2$)$_m$—(CHR$^5$)$_n$—R$^6$,
wherein R$^1$, R$^4$, R$^5$, R$^6$, m and n are as defined above, one of R$^{2'}$ and R$^{3'}$ is OH and the other of R$^{2'}$ and R$^{3'}$ is hydrogen, lower-alkyl, or halogen, and A is hydrogen or a protecting group or
reacting a compound of formula (II)

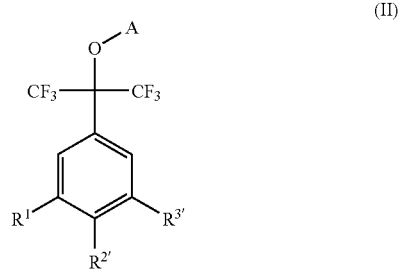

with a compound LG-CHR$^4$—(CH$_2$)$_m$—(CHR$^5$)$_n$—R$^6$
wherein R$^1$, R$^4$, R$^5$, R$^6$, m and n are as defined above, one of R$^{2'}$ and R$^{3'}$ is OH and the other of R$^{2'}$ and R$^{3'}$ is hydrogen, lower-alkyl, or halogen, LG is a leaving group (such as I, Br, Cl, OTf, OMs, OTs) and A is hydrogen or a protecting group.

The reaction of a compound of formula (II) with a compound HO—CHR⁴—(CH$_2$)$_m$—(CHR⁵)$_n$—R⁶ or with LG-CHR⁴—(CH$_2$)$_m$—(CHR⁵)$_n$—R⁶ and cleavage of the protecting group A if necessary can be performed under reaction conditions well known to the person skilled in the art. Such reactions of a phenol (II) can conveniently be carried out either under Mitsunobu conditions with an alcohol HO—CHR⁴—(CH$_2$)$_m$—(CHR⁵)$_n$—R⁶ in the presence of DEAD or DIAD and Ph$_3$P in a solvent such as THF at a suitable temperature or with an alkylating agent LG-CHR⁴—(CH$_2$)$_m$—(CHR⁵)$_n$—R⁶ with bases such as Cs$_2$CO$_3$, K$_2$CO$_3$ optionally in the presence of KI or NaI in inert solvents such as acetone, THF, DMF or DMA.

The present invention also relates to compounds of formula (I) as defined above, when prepared by a process as described above.

The compounds of formula (I) can be prepared by methods known in the art or as described below. Unless otherwise indicated, the substituents R¹, R², R³, R⁴, R⁵, R⁶, R⁷, m, and n are as described above.

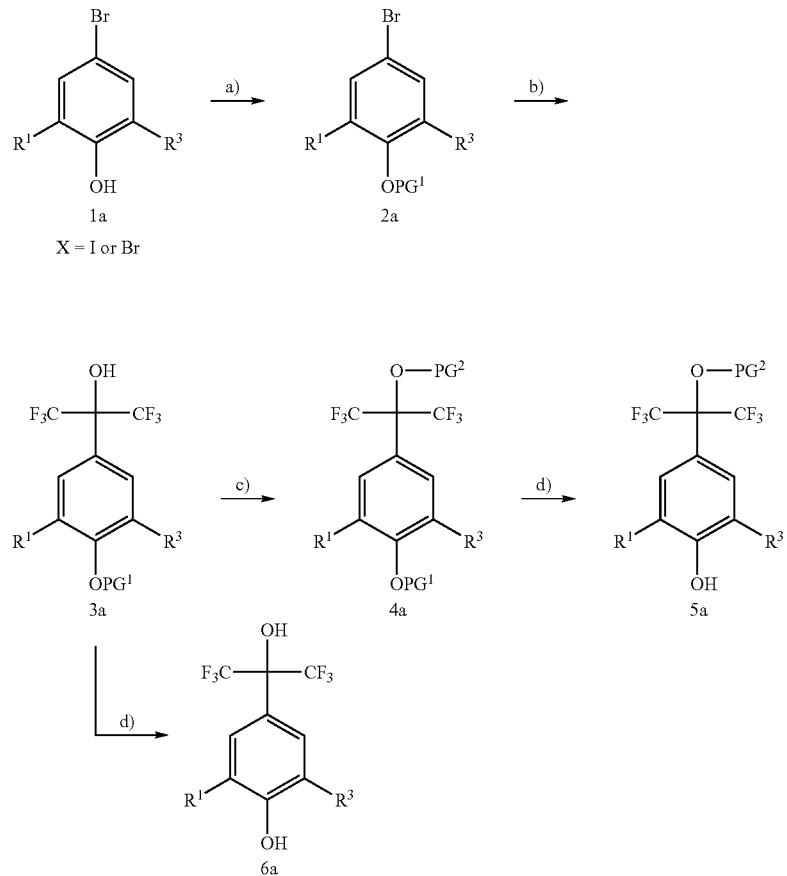

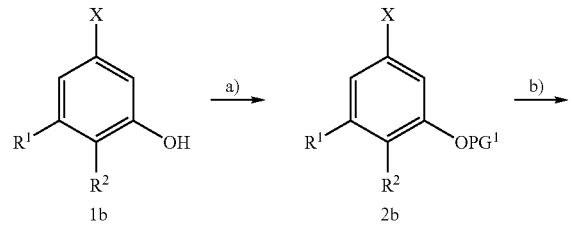

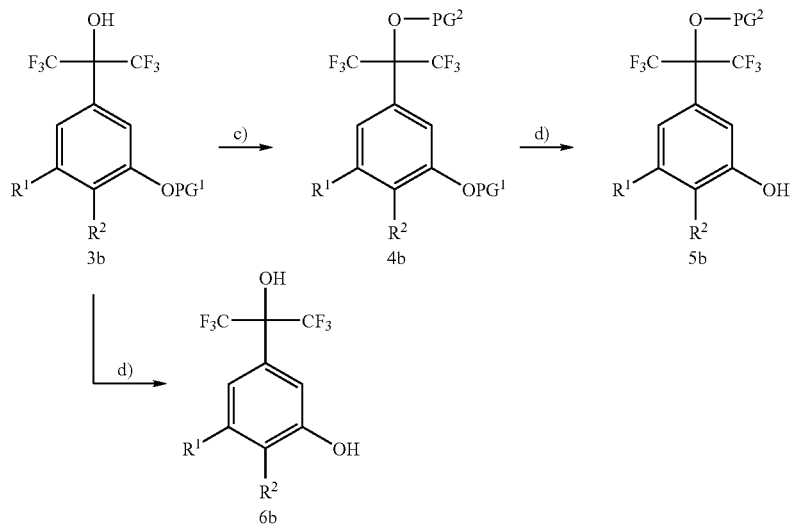
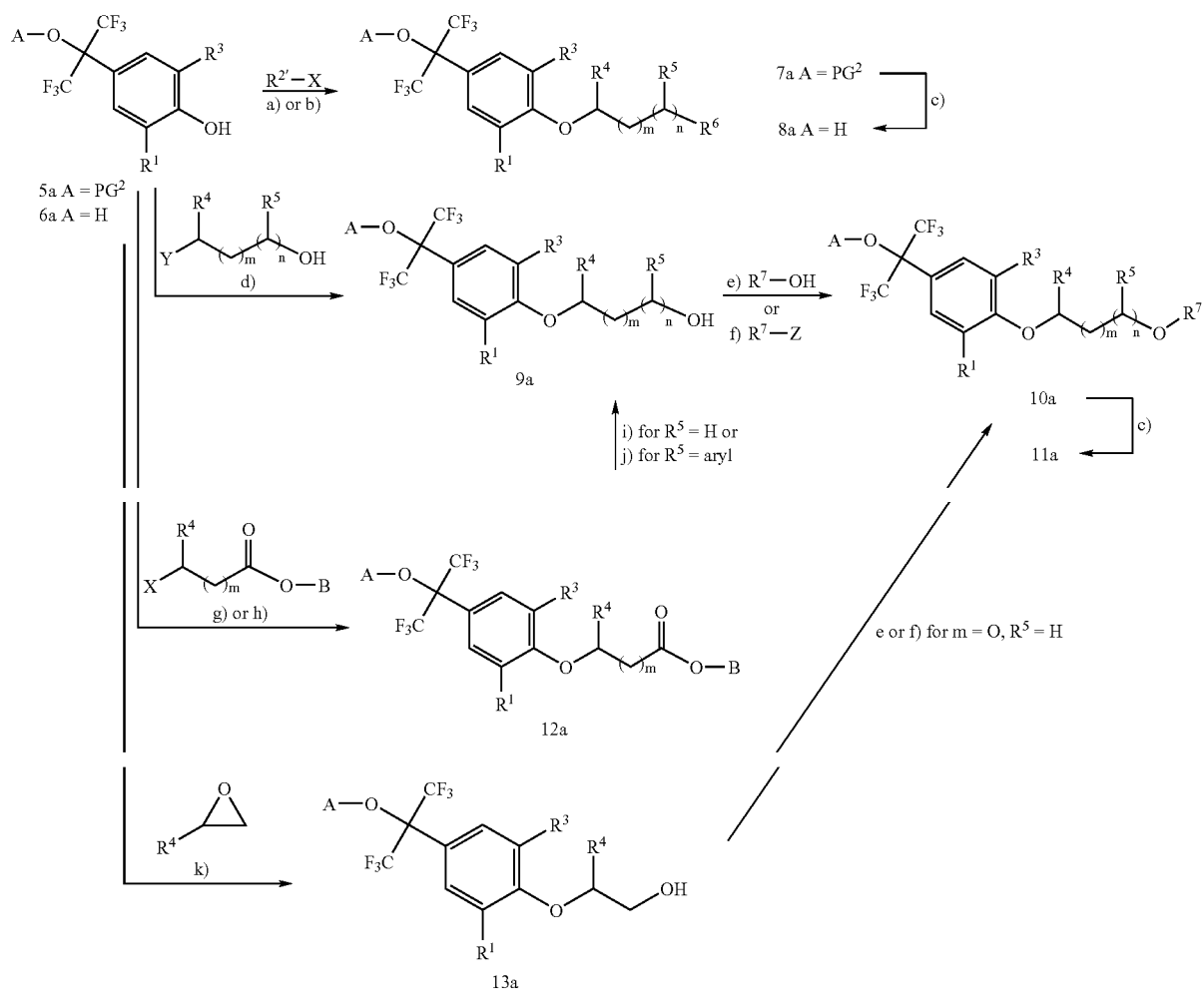
Scheme 2a

Scheme 2b

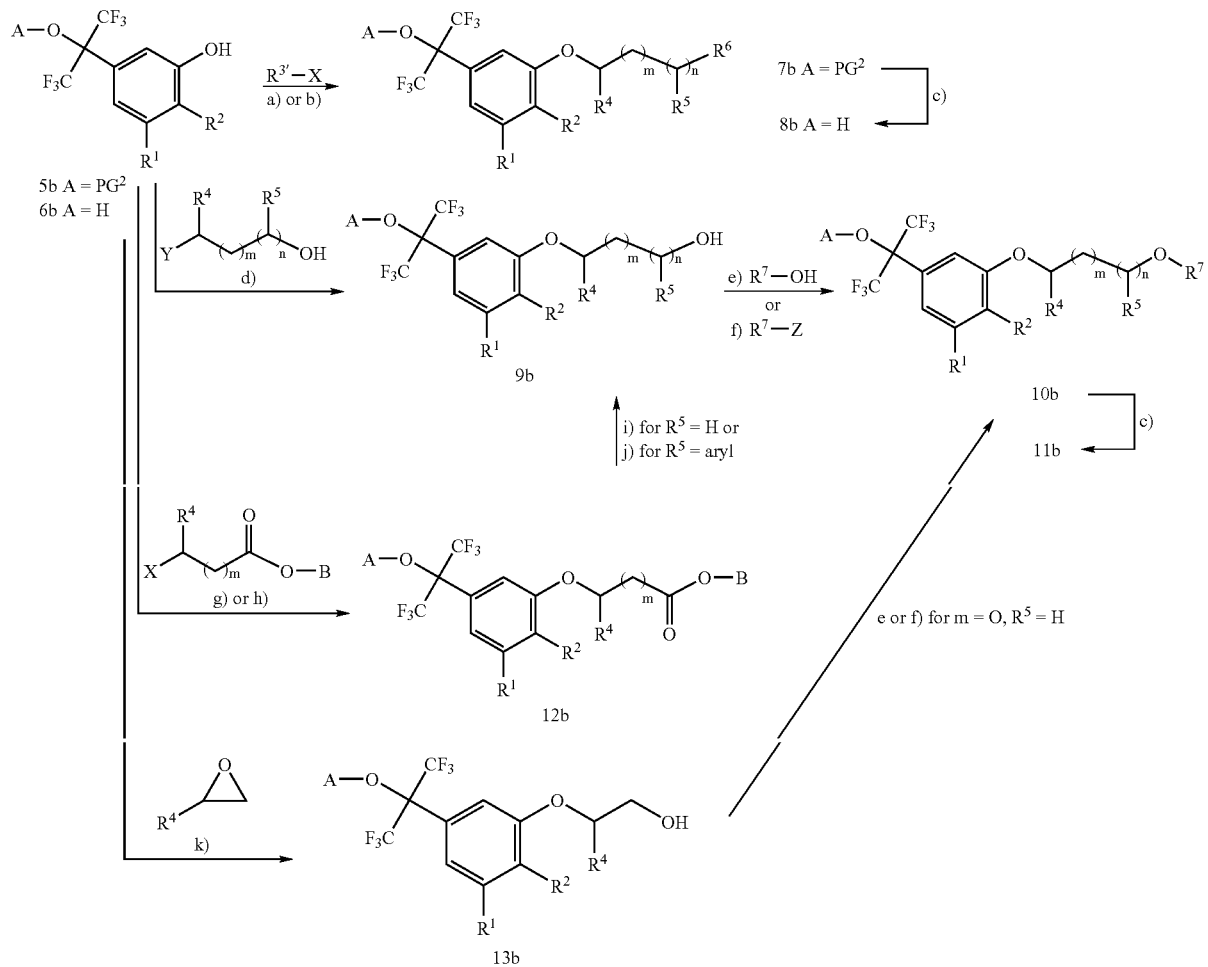

The preparation of starting materials for the synthesis of compounds of formula (I) is illustrated in schemes 1a/1b. Bromophenol derivatives 1a or 1b are transformed into the suitably protected derivatives 2a or 2b by treatment with e.g. silylating agents such as t-BuMe$_2$SiCl or t-BuPh$_2$SiCl in solvents such as DMF, or THF in the presence of a base such as imidazole or triethylamine at temperatures between 0° C. and room temperature (step a). 2a or 2b may be converted to the derivatives 3a or 3b by treatment with n-BuLi or t-BuLi in solvents such as THF or ether, followed by reaction with hexafluoro acetone at low temperature, e.g. −78° C. (step b). The compounds 3a or 3b may be O-protected by a Mitsunobu reaction with reagents such as benzyl alcohol or 4-methoxybenzyl alcohol (PMB—OH) in THF in the presence of triphenylphosphine and DEAD or DIAD to give 4a or 4b, respectively (step c). Cleavage of the protecting group PG$^1$ may be achieved by treatment of the compound 3a, 3b, 4a or 4b with TBAF in THF or 48% aq. HBr, KF in DMF to yield the desired building blocks 5a, 5b, 6a or 6b, respectively (step d).

Schemes 2a/2b depict the synthesis of the final products. Treatment of phenol 5a or 5b with R$^{2'}$—X or R$^{3'}$—X (with R$^{2'}$ or R$^{3'}$=CHR$^4$—(CH$_2$)$_m$—(CHR$^5$)$_n$—R$^6$) under Mitsunobu conditions for X=OH with e.g. Ph$_3$P, DEAD or DIAD in a solvent such as THF gives 7a or 7b (step a). Alternatively, 5a or 5b may be treated with alkylating agents R$^{2'}$—X or R$^{3'}$—X in which X is a leaving group such as Cl, Br, I, MsO, TsO, or TfO. These reactions are performed in the presence of a base such as Cs$_2$CO$_3$ or K$_2$CO$_3$ in inert solvents such as acetone, dioxane, DMF or DMA optionally in the presence of KI or NaI to give 7a or 7b (step b). Cleavage of the protecting group PG$^2$ may be accomplished by hydrogenation in the presence of a catalyst such as Pd/C in a solvent such as EtOAc or alcohols (EtOH, MeOH) for PG$^2$=Bn or PMB. An alternative method for cleavage of the PMB group may be the treatment of 7a or 7b with DDQ in CH$_2$Cl$_2$ or dichloroethane in the presence of H$_2$O at temperatures between −20° C. and reflux or the treatment with ceric ammonium nitrate in acetonitrile/water to give 8a (step c). In some cases the direct conversion of 6a or 6b (A=H) to 8a or 8b respectively, may be achieved under Mitsunobu conditions with the alcohols R$^{2'}$—X or R$^{3'}$—X.

Alternatively, the final product may be assembled in several steps. Treatment of the phenol 5a or 5b with Y—CHR$^4$—(CH$_2$)$_m$—(CHR$^5$)$_n$—OH (Y=leaving group such as e.g. Cl, Br, I, MsO, TsO, or TfO) in the presence of bases such as Cs$_2$CO$_3$ or K$_2$CO$_3$ in inert solvents such as acetone, dioxane, DMF or DMA optionally in the presence of KI or NaI gives alcohol 9a or 9b (step d). 9a or 9b can be converted to 10a or 10b by reaction with aryl or heteroaryl derivative $R^7$—OH using Mitsunobu conditions ($Ph_3P$, DEAD or DIAD) in a solvent such as THF (step e). Alternatively, the alcohol 9a or 9b can be subjected to a nucleophilic aromatic substitution reaction with $R^7$-Z wherein Z is a leaving group such as F, Br or I or to a transition metal catalyzed coupling reaction with $R^7$-Z wherein Z is Cl, Br, I or OTf (step f). Deprotection to the final product 11a or 11b may be accomplished as described above by hydrogenation (for $PG^2$=Bn or PMB) or by oxidative cleavage (for $PG^2$=PMB) with DDQ in $CH_2Cl_2$ or dichloromethane, dichloroethane and water at temperatures between −20° C. and reflux or with ceric ammonium nitrate in acetonitrile and water (step c).

Another procedure consists of the treatment of 5a or 5b with an ester of the formula X—$CHR^4$—$(CH_2)_m$—$CO_2$—B under Mitsunobu conditions for X=OH with $Ph_3P$, DEAD or DIAD in a solvent such as THF to give 12a or 12b (step g). Alternatively, 5a or 5b may be treated with X—$CHR^4$—$(CH_2)_m$—$CO_2$—B under alkylating conditions for X=leaving group such as e.g. Cl, Br, I, MsO, TsO, or TfO with bases such as $Cs_2CO_3$ or $K_2CO_3$ in acetone, dioxane, DMF or DMA in the presence of KI or NaI to give 12a or 12b (step h). Reduction of the ester 12a or 12b with sodium borohydride in a solvent such as THF, methanol or ethanol or mixtures thereof yields 9a or 9b (for $R^5$=H, step i). Alternatively, the ester may be converted to derivative 9a or 9b (for $R^5 \neq H$, step j) in two or three steps. Reduction of the ester to an aldehyde can be accomplished directly by e.g. DIBAH or by a reduction to the alcohol by e.g. $LiAlH_4$ and subsequent reoxidation to the aldehyde. The reaction of the aldehyde with a Grignard reagent $R^5$—MgBr or $R^5$—MgCl or organolithium reagent $R^5$—Li gives derivative 9a or 9b (for $R^5$=H, step j). 9a may be converted to 10a and 11a as described above (steps e,c or f,c).

If 5a or 5b is treated with a $R^4$ substituted oxirane in a solvent such as dioxane, DMF or DMA in the presence of bases such as $Cs_2CO_3$ or $K_2CO_3$ under microwave conditions (step k) alcohol 13a or 13b can be isolated. These alcohols 13a or 13b can be converted to 10a or 10b and 11a or 11b (with m=0 and $R^5$=H) respectively, using the reaction conditions described previously for steps e and c or f and c.

A large number of compounds X—$(CHR^4)(CH_2)_m(CHR^5)_nR^6$, in which $R^4$ to $R^6$, m, n, and X are defined as above, are commercially available. If not, they may be prepared from a related commercially available starting material such as e.g. an alcohol HO—$(CHR^4)$—$(CH_2)_m(CHR^5)_nR^6$, an ester alkylOOC—$(CH_2)_m$—$(CHR^5)_nR^6$, or a carboxylic acid HOOC—$(CH_2)_m$—$(CHR^5)_nR^6$ according to standard literature procedures commonly known to those skilled in the art. $R^4$ substituted oxiranes may be prepared by treatment of $R^4CH$=$CH_2$ with a commonly used epoxidizing agent such as m-CPBA. Many of the X—$(CHR^4)(CH_2)_m(CHR^5)_nR^6$ wherein $R^4$, $R^5$=H, and $R^6$=heteroaryl may be prepared according to literature procedures (e.g. Binggeli et al. WO2004031162, WO200292084 and WO97019311, Boehringer et al. WO2003037327, Bouillot et al. WO2004006922; Morita et al., JP9095482; Cynkowski et al., J. Chem. Soc. Chem. Commun., 1995, 2335-2336; Kodama et al., U.S. Pat. No. 6,472,386; Faul et al., Heterocycles, 2001, 55 (4), 689-704, Ackermann et al. WO200236584, Adams et al. WO9728137).

After preparation of derivatives 7a, 7b or 10a, 10b according to the synthetic descriptions above, functional groups present in $R^6$ or $R^7$ may be converted further prior to cleavage of the protecting group A. Examples for typical transformations of such functional groups are summarized below:

Ester moieties may be hydrolysed to the corresponding acids by treatment with LiOH, NaOH or KOH in solvents such as THF, methanol or ethanol. The resulting acids may be converted to amides by treatment with an amine $NHR^aR^b$ in the presence of a coupling reagent such as N,N-dicylohexylcarbo-diimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU) and 1-hydroxybenzo-triazole (HOBT) and a base such as Huenigs base, $Et_3N$ or NMM (N-methylmorpholine) in a solvent such as THF, ether or dichloromethane. Reduction of the esters with reducing agents such as $NaBH_4$, $LiAlH_4$ in solvents such as MeOH or THF may give the corresponding hydroxyalkyl residues. Alternatively, the conversions may be carried out with the unprotected derivatives 8a, 8b, 11a or 11b, respectively.

Prior to the derivatizations of the functional group on $R^6$ or $R^7$, sensitive functional groups may be suitably protected (e.g. silylation of a hydroxy group) and deprotected again when desired or required (as described e.g. in "Protective Groups in Organic Synthesis" by T. W. Greene and P. G. M. Wuts, $2^{nd}$ Ed., 1991, Wiley N.Y.).

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula (I) by treatment with physiologically compatible bases.

The conversion of compounds of formula (I) into pharmaceutically acceptable esters can be carried out e.g. by treatment of suited amino or hydroxy groups present in the molecules with an carboxylic acid such as acetic acid, with a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU) to produce the carboxylic ester or carboxylic amide.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment and prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant. The invention likewise embraces compounds as described above for use as therapeutically active substances, especially as therapeutically active substances for the treatment and/or prophylaxis of diseases which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease.

The invention also relates to the use of compounds as described above for the preparation of medicaments for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, skin diseases, colitis, pancreatitis, cholestasis of the liver, fibrosis of the liver, macular degeneration and/or Alzheimer's disease. Such medicaments comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia, especially prevention and/or treatment of atherosclerotic diseases or dyslipidemia.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Abbreviations:
n-BuLi=n-butyl lithium, $CH_2Cl_2$=dichloromethane, DDQ=2,3-dichloro-5,6-dicyano-1,4-benzoquinone, DEAD=diethyl azodicarboxylate, DIAD=di-isopropyl azodicarboxylate, DMF=dimethylformamide, EDCI=N-(3-dimethylaminopropyl)-N'-ethylcarbodiimide hydrochloride, EtOAc=ethyl acetate, EtOH=ethanol, $Et_2O$=diethyl ether, MeOH=methanol, HOBT=1-hydroxybenzo-triazole, Huenigsbase=$iPr_2NEt$, N-ethyldiisopropylamine, NMM=N- metylmorpholine, TBAF=tetra n-butylammonium fluoride, TBDMSCl=tert-butyldimethylsilyl chloride, TFA=trifluoroacetic acid, THF=tetrahydrofuran.

General Remarks

All reactions were performed under argon.

Example 1

4-[2,2,2-Trifluoro-1-(4-methoxy-benzyloxy)-1-trifluoromethyl-ethyl]-phenol 1.1

At 0° C., to 10 g (57.81 mmol) of 4-bromo-phenol in 100 ml of DMF were added 4.33 g (63.6 mmol) of imidazole and 9.58 g (63.6 mmol) of TBDMSCl in 30 ml of DMF. The mixture was stirred at room temperature overnight. A saturated solution of $NaHCO_3$ was added, and the product was extracted with diethyl ether (3×). The organic phase was washed with water and brine, and dried ($Na_2SO_4$). After filtration and evaporation of the solvent 16.57 g (99%) of (4-bromo-phenoxy)-tert-butyl-dimethyl-silane were isolated as a colorless liquid, MS: 286 (M, 1Br)$^+$.

1.2

At −78° C., a solution of 16.57 g (57.7 mmol) of (4-bromo-phenoxy)-tert-butyl-dimethyl-silane in 140 ml of THF was treated with 43.6 ml (69.8 mmol) of n-BuLi (ca 1.6 M in hexane). After 30 min at this temperature hexafluoroacetone was bubbled into the solution (very exothermic reaction). Stirring was continued for additional 30 min at −78° C., and a solution of $NH_4Cl$ was added to the mixture. The phases were separated and the product was extracted with EtOAc (3×). The combined organic phases were washed with brine, dried ($Na_2SO_4$), filtered and evaporated. Purification by flash-chromatography on silica gel (n-heptane/EtOAc 97:3 to 9:1) gave 8.5 g (40%) of 2-[4-(tert-butyl-dimethyl-silanyloxy)-phenyl]-1,1,1,3,3,3-hexafluoro-propan-2-ol as a yellow liquid, MS: 374 (M)$^+$.

1.3

To a solution of 4.1 g (29.6 mmol) of 4-methoxybenzyl alcohol in 100 mL of THF was added 7.76 g (29.6 mmol) of triphenylphosphine and 8.53 g (22.8 mmol) of 2-[4-(tert-butyl-dimethyl-silanyloxy)-phenyl]-1,1,1,3,3,3-hexafluoro-propan-2-ol at room temperature. The reaction mixture was cooled to 0° C. and 5.7 mL (29.6 mmol) of diisopropylazo dicarboxylate were added. The solution was stirred at room temperature overnight, a solution of $NH_4Cl$ was added and the inorganic layer was extracted with ethyl acetate. The combined layers were washed with brine, and dried ($Na_2SO_4$), filtered and evaporated. Column chromatography with ethyl acetate/n-heptane 1:99 as eluent yielded 8.39 g (74%) of tert-butyl-dimethyl-{4-[2,2,2-trifluoro-1-(4-methoxy-benzyloxy)-1-trifluoromethyl-ethyl]-phenoxy}-silane as a light yellow liquid, MS: 494 (M)$^+$.

1.4

8.39 g (17.0 mmol) of tert-butyl-dimethyl-{4-[2,2,2-trifluoro-1-(4-methoxy-benzyloxy)-1-trifluoromethyl-ethyl]-phenoxy}-silane was dissolved in 70 mL of THF and 25.4 ml (25.4 mmol) of 1M TBAF solution in THF was added at 0° C. The mixture was stirred at room temperature overnight, a 1M $KHSO_4$ solution was added and the product was extracted with ethyl acetate (2×). The organic phase was washed with brine, dried ($Na_2SO_4$), filtered and evaporated. Column chromatography on silica gel with n-heptane/ethyl acetate 5:1 as eluent yielded 4-[2,2,2-trifluoro-1-(4-methoxy-benzyloxy)-1-trifluoromethyl-ethyl]-phenol as a yellow liquid, MS: 379 (M−H)$^−$.

Example 2

2-Methyl-4-[2,2,2-trifluoro-1-(4-methoxy-benzyloxy)-1-trifluoromethyl-ethyl]-phenol In analogy to example 1.1-1.4, from 4-bromo-2-methylphenol was prepared 2-methyl-4-[2,2,2-trifluoro-1-(4-methoxy-benzyloxy)-1-trifluoromethyl-ethyl]-phenol as a white solid, MS: 393 (M−H)$^−$.

Example 3

2-Chloro-4-[2,2,2-trifluoro-1-(4-methoxy-benzyloxy)-1-trifluoromethyl-ethyl]-phenol In analogy to example 1.1-1.4, from 4-bromo-2-chlorophenol was prepared 2-chloro-4-[2,2,2-trifluoro-1-(4-methoxy-benzyloxy)-1-trifluoromethyl-ethyl]-phenol as an off-white solid, MS: 414 (M, 1Cl)$^+$.

Example 4

2,6-Dimethyl-4-[2,2,2-trifluoro-1-(4-methoxy-benzyloxy)-1-trifluoromethyl-ethyl]-phenol In analogy to example 1.1-1.4, from 4-bromo-2,6-dimethyl-phenol was prepared 2,6-dimethyl-4-[2,2,2-trifluoro-1-(4-methoxy-benzyloxy)-1-trifluoromethyl-ethyl]-phenol as a yellow solid, MS: 407 (M−H)$^−$.

Example 5

3-[2,2,2-Trifluoro-1-(4-methoxy-benzyloxy)-1-trifluoromethyl-ethyl]-phenol

In analogy to example 1.1-1.4, from 3-bromo-phenol was prepared 3-[2,2,2-trifluoro-1-(4-methoxy-benzyloxy)-1-trifluoromethyl-ethyl]-phenol as a white semisolid, MS: 380 (M)$^+$.

Example 6

4-(2,2,2-Trifluoro-1-hydroxy-1-trifluoromethyl-ethyl)-phenol

In analogy to example 1.4, from 2-[4-(tert-butyl-dimethyl-silanyloxy)-phenyl]-1,1,1,3,3,3-hexafluoro-propan-2-ol (example 1.2) was prepared 4-(2,2,2-trifluoro-1-hydroxy-1-trifluoromethyl-ethyl)-phenol as a white crystalline solid, MS: 259 (M−H)$^−$.

Example 7

2-(4-{3-[3-(4-Bromo-phenyl)-benzo[d]isothiazol-6-yloxy]-propoxy}-phenyl)-1,1,1,3,3,3-hexafluoro-propan-2-ol 100 mg (0.23 mmol) of 3-(4-bromo-phenyl)-benzo[d]isothiazol-6-ol (CAS 423159-55-1, prepared as described in WO 2002036584) in 2 ml of acetone were treated with 67 mg (0.22 mmol) of 4-(2,2,2-trifluoro-1-hydroxy-1-trifluoromethyl-ethyl)-phenol (example 6), 76 mg (0.2 mmol) of $Cs_2CO_3$ and 8 mg (0.05 mmol) of potassium iodide. The reaction mixture was stirred at ambient temperature for 2.5 d, at 45° C. for 4 h, and then was diluted with dichloromethane. The organic phase was washed with water and brine, dried (Na$_2$SO$_4$) and evaporated. The crude product was purified by column chromatography on silica gel to yield 40 mg (28%) 2-(4-{3-[3-(4-bromo-phenyl)-benzo[d]isothiazol-6-yloxy]-propoxy}-phenyl)-1,1,1,3,3,3-hexafluoro-propan-2-ol as a colorless solid, MS: 604 (M−H, 1Br)$^−$.

Example 8

3-(3-{3-[3-(2,2,2-Trifluoro-1-hydroxy-1-trifluoromethyl-ethyl)-phenoxy]-propoxy}-phenyl)-propionic acid ethyl ester 8.1

1.12 g (2.9 mmol) of 3-[2,2,2-trifluoro-1-(4-methoxy-benzyloxy)-1-trifluoromethyl-ethyl]-phenol (example 5) in 20 ml of acetone were treated with 0.51 mL (5.9 mmol) of 3-bromo-1-propanol in the presence of 1.9 g (5.9 mmol) Cs$_2$CO$_3$ and 245 mg (1.5 mmol) of potassium iodide. The reaction mixture was stirred at 50° C. overnight, filtered and evaporated. The crude product was redissolved in EtOAc and a 1M KHSO$_4$ solution, the phases were separated and the inorganic one extracted with EtOAc. The combined organic phases were washed with brine, dried (Na$_2$SO$_4$) and the solvent was evaporated. Column chromatography on silica gel yielded 1.1 g (84%) of 3-{3-[2,2,2-trifluoro-1-(4-methoxy-benzyloxy)-1-trifluoromethyl-ethyl]-phenoxy}-propan-1-ol as a colorless liquid, MS: 438 (M)$^+$.

8.2

150 mg (0.3 mmol) of 3-{3-[2,2,2-trifluoro-1-(4-methoxy-benzyloxy)-1-trifluoromethyl-ethyl]-phenoxy}-propan-1-ol and 73 mg (0.38 mmol) of 3-(3-hydroxy-phenyl)-propionic acid ethyl ester (CAS 34708-60-6) in 4 mL of THF were treated with 117 mg (0.44 mmol) of triphenylphosphine. The solution was cooled to 0° C. and treated with 88 μL (0.44 mmol) of DIAD. The mixture was stirred at room temperature overnight, the solvent was evaporated and the crude mixture was purified by column chromatography on silica gel with a gradient of EtOAc/n-heptane 1:5 to 1:3 to yield 110 mg (52%) of 3-[3-(3-{3-[2,2,2-trifluoro-1-(4-methoxy-benzyloxy)-1-trifluoromethyl-ethyl]-phenoxy}-propoxy)-phenyl]-propionic acid ethyl ester as a colorless liquid, MS: 614 (M)$^+$.

8.3

100 mg (0.16 mmol) of 3-[3-(3-{3-[2,2,2-trifluoro-1-(4-methoxy-benzyloxy)-1-trifluoromethyl-ethyl]-phenoxy}-propoxy)-phenyl]-propionic acid ethyl ester in 10 mL of EtOAc were hydrogenated in the presence of 60 mg of 10% Pd/C. After removal of the catalyst and evaporation of the solvent, the residue was purified by column chromatography on silica gel with a gradient of EtOAc/n-heptane 1:5 to 1:3 to yield 64 mg (80%) of 3-(3-{3-[3-(2,2,2-trifluoro-1-hydroxy-1-trifluoromethyl-ethyl)-phenoxy]-propoxy}-phenyl)-propionic acid ethyl ester as a colorless oil, MS: 493 (M−H)$^−$.

Example 9 rac (4-{1-Phenyl-2-[3-(2,2,2-trifluoro-1-hydroxy-1-trifluoromethyl-ethyl)-phenoxy]-ethoxy}-phenyl)-acetic acid methyl ester 9.1

To 1 g (2.6 mmol) of 3-[2,2,2-trifluoro-1-(4-methoxy-benzyloxy)-1-trifluoromethyl-ethyl]-phenol (example 5) in 8 mL of dioxane were added 1.0 mL (8.8 mmol) of 2-phenyl-oxirane. The reaction was split in 2 portions. To each of those was added 4.28 g (13.1 mmol) of Cs$_2$CO$_3$ and each reaction mixture was treated for 30 min at 130° C. in the microwave. The mixtures were combined and water and ether were added. The aqueous phase was extracted with ether and the combined organic phases were washed with brine and dried (Na$_2$SO$_4$). After evaporation of the solvent the crude products were separated by column chromatography to give 810 mg (62%) of rac 1-phenyl-2-{3-[2,2,2-trifluoro-1-(4-methoxy-benzyloxy)-1-trifluoromethyl-ethyl]-phenoxy}-ethanol as light yellow oil, MS: 500 (M)$^+$, and 250 mg (19%) of rac 2-phenyl-2-{3-[2,2,2-trifluoro-1-(4-methoxy-benzyloxy)-1-trifluoromethyl-ethyl]-phenoxy}-ethanol as light yellow oil, MS: 500 (M)$^+$.

9.2

In analogy to example 8.2, from rac 1-phenyl-2-{3-[2,2,2-trifluoro-1-(4-methoxy-benzyloxy)-1-trifluoromethyl-ethyl]-phenoxy}-ethanol and methyl 4-hydroxyphenyl-acetate was prepared rac [4-(1-phenyl-2-{3-[2,2,2-trifluoro-1-(4-methoxy-benzyloxy)-1-trifluoromethyl-ethyl]-phenoxy}-ethoxy)-phenyl]-acetic acid methyl ester as a colorless oil, MS: 648(M)$^+$.

9.3

In analogy to example 8.3, from rac [4-(1-phenyl-2-{3-[2,2,2-trifluoro-1-(4-methoxy-benzyloxy)-1-trifluoromethyl-ethyl]-phenoxy}-ethoxy)-phenyl]-acetic acid methyl ester was prepared rac (4-{1-phenyl-2-[3-(2,2,2-trifluoro-1-hydroxy-1-trifluoromethyl-ethyl)-phenoxy]-ethoxy}-phenyl)-acetic acid methyl ester as a colorless oil, MS: 527 (M−H)$^−$.

Example 10 rac (4-{1-Phenyl-2-[3-(2,2,2-trifluoro-1-hydroxy-1-trifluoromethyl-ethyl)-phenoxy]-ethoxy}-phenyl)-acetic acid 40 mg (0.08 mmol) of rac (4-{1-phenyl-2-[3-(2,2,2-trifluoro-1-hydroxy-1-trifluoromethyl-ethyl)-phenoxy]-ethoxy}-phenyl)-acetic acid methyl ester (example 9) in 1 mL of THF were treated with 0.76 mL of 1M LiOH at room temperature for 2 h. 1M KHSO$_4$ solution was added, the phases were separated, and the inorganic one was extracted with EtOAc. The combined organic phases were washed with brine, dried (Na$_2$SO$_4$) and evaporated. The crude product was purified by column chromatography to give 29 mg (74%) of rac (4-{1-phenyl-2-[3-(2,2,2-trifluoro-1-hydroxy-1-trifluoromethyl-ethyl)-phenoxy]-ethoxy}-phenyl)-acetic acid as a colorless oil, MS: 513 (M−H)$^−$.

Example 11 rac 4-{1-Phenyl-2-[4-(2,2,2-trifluoro-1-hydroxy-1-trifluoromethyl-ethyl)-phenoxy]-ethoxy}-benzoic acid methyl ester 11.1

In analogy to example 10.1, from 4-hydroxy-benzoic acid methyl ester and rac 2-phenyl-oxirane was prepared rac 4-(2-hydroxy-1-phenyl-ethoxy)-benzoic acid methyl ester, MS: 273 (M)$^+$.

11.2

In analogy to example 8.2, from 4-[2,2,2-trifluoro-1-(4-methoxy-benzyloxy)-1-trifluoromethyl-ethyl]-phenol and rac 4-(2-hydroxy-1-phenyl-ethoxy)-benzoic acid methyl ester was prepared rac 4-(1-phenyl-2-{4-[2,2,2-trifluoro-1-(4-methoxy-benzyloxy)-1-trifluoromethyl-ethyl]-phenoxy}-ethoxy)-benzoic acid methyl ester as a yellow oil, MS: 634 (M)$^+$.

11.3

76 mg (0.12 mmol) of rac 4-(1-phenyl-2-{4-[2,2,2-trifluoro-1-(4-methoxy-benzyloxy)-1-trifluoromethyl-ethyl]-phenoxy}-ethoxy)-benzoic acid methyl ester in 4 ml of a mixture of acetonitrile:water (9:1) were treated with 250 mg (0.46 mmol) of ceric ammonium nitrate at room temperature overnight. An additional 100 mg (0.18 mmol) of ceric ammonium nitrate were added and stirring was continued for 3 h. EtOAc and 1M KHSO$_4$ were added and the phases were separated. The inorganic one was extracted with EtOAc, the combined organic phases were washed with brine and dried (Na$_2$SO$_4$) and evaporated. Column chromatography on ISOLUTE Flash NH$_2$ with a gradient of EtOAc/n-heptane to EtOAc gave 30 mg (48%) of rac 4-{1-phenyl-2-[4-(2,2,2-trifluoro-1-hydroxy-1-trifluoromethyl-ethyl)-phenoxy]-ethoxy}-benzoic acid methyl ester as a colorless oil, MS: 513 (M–H)$^-$.

Example 12

4-{2-[4-(2,2,2-Trifluoro-1-hydroxy-1-trifluoromethyl-ethyl)-phenoxy]-ethoxy}-benzoic acid methyl ester 12.1

In analogy to example 8.1, from 4-hydroxy-benzoic acid methyl ester and 2-bromo-ethanol was prepared 4-(2-hydroxy-ethoxy)-benzoic acid methyl ester as a colorless oil, MS: 197 (M+H)$^+$.

12.2

In analogy to example 11.2 (8.2) and 11.3, from 4-[2,2,2-trifluoro-1-(4-methoxy-benzyloxy)-1-trifluoromethyl-ethyl]-phenol and 4-(2-hydroxy-ethoxy)-benzoic acid methyl ester was prepared 4-{2-[4-(2,2,2-trifluoro-1-hydroxy-1-trifluoromethyl-ethyl)-phenoxy]-ethoxy}-benzoic acid methyl ester as a white semisolid, MS: 437 (M–H)$^-$.

Example 13

2-(4-Benzyloxy-3-chloro-phenyl)-1,1,1,3,3,3-hexafluoro-propan-2-ol 13.1

100 mg (0.2 mmol) of 2-chloro-4-[2,2,2-trifluoro-1-(4-methoxy-benzyloxy)-1-trifluoromethyl-ethyl]-phenol (example 3) in 4 ml of acetone were treated with 47 mg (0.3 mmol) of benzyl bromide, 157 mg (0.5 mmol) of Cs$_2$CO$_3$ and 4 mg (0.025 mmol) of potassium iodide. The reaction mixture was stirred at 50° C. overnight, cooled to room temperature, filtered and the solvent was evaporated. The residue was dissolved in EtOAc and water, the phases were separated and the inorganic one was extracted with EtOAc. The combined organic phases were washed with brine, dried (Na$_2$SO$_4$) and evaporated to give 82 mg (67%) of crude 1-benzyloxy-2-chloro-4-[2,2,2-trifluoro-1-(4-methoxy-benzyloxy)-1-trifluoromethyl-ethyl]-benzene.

13.2

82 mg (0.2 mmol) of crude 1-benzyloxy-2-chloro-4-[2,2,2-trifluoro-1-(4-methoxy-benzyloxy)-1-trifluoromethyl-ethyl]-benzene were treated with 3 mL of a mixture of dichloromethane/trifluoroacetic acid (1:3) at room temperature for 1 h. The solvent was evaporated and the residue was redissolved in a mixture of diethyl ether and a solution of Na$_2$CO$_3$. The inorganic phase was extracted with diethyl ether and the combined organic phases were washed with brine and dried (Na$_2$SO$_4$). After filtration and evaporation of the solvent, the crude product was purified by column chromatography to give 7.3 mg (12%) of 2-(4-benzyloxy-3-chloro-phenyl)-1,1,1,3,3,3-hexafluoro-propan-2-ol as a yellow gum, MS: 383 (M–H, 1Cl)$^-$.

Example 14

2-(4-Benzyloxy-3-methyl-phenyl)-1,1,1,3,3,3-hexafluoro-propan-2-ol

In analogy to example 13.1-13.2, from 2-methyl-4-[2,2,2-trifluoro-1-(4-methoxy-benzyloxy)-1-trifluoromethyl-ethyl]-phenol (example 2) and benzyl bromide was prepared 2-(4-benzyloxy-3-methyl-phenyl)-1,1,1,3,3,3-hexafluoro-propan-2-ol as a light yellow gum, MS: 363 (M–H)$^-$.

Example 15

2-(3-Benzyloxy-phenyl)-1,1,1,3,3,3-hexafluoro-propan-2-ol

In analogy to example 13.1-13.2, from 3-[2,2,2-trifluoro-1-(4-methoxy-benzyloxy)-1-trifluoromethyl-ethyl]-phenol (example 5) and benzyl bromide was prepared 2-(3-benzyloxy-phenyl)-1,1,1,3,3,3-hexafluoro-propan-2-ol as an off-white solid, MS: 349 (M–H)$^-$.

Example 16

2-(4-Benzyloxy-3,5-dimethyl-phenyl)-1,1,1,3,3,3-hexafluoro-propan-2-ol

In analogy to example 13.1-13.2, from 2,6-dimethyl-4-[2,2,2-trifluoro-1-(4-methoxy-benzyloxy)-1-trifluoromethyl-ethyl]-phenol (example 4) and benzyl bromide was prepared 2-(4-benzyloxy-3,5-dimethyl-phenyl)-1,1,1,3,3,3-hexafluoro-propan-2-ol as a light yellow solid, MS: 377 (M–H)$^-$.

Example 17

2-(4-Benzyloxy-phenyl)-1,1,1,3,3,3-hexafluoro-propan-2-ol

In analogy to example 13.1-13.2, from 4-[2,2,2-trifluoro-1-(4-methoxy-benzyloxy)-1-trifluoromethyl-ethyl]-phenol (example 1) and benzyl bromide was prepared 2-(4-benzyloxy-phenyl)-1,1,1,3,3,3-hexafluoro-propan-2-ol as an off-white solid, MS: 349 (M–H)$^-$.

Example 18

(4-{3-[2-Methyl-4-(2,2,2-trifluoro-1-hydroxy-1-trifluoromethyl-ethyl)-phenoxy]-propoxy}-phenyl)-acetic acid methyl ester 18.1

In analogy to example 8.1, from 2-methyl-4-[2,2,2-trifluoro-1-(4-methoxy-benzyloxy)-1-trifluoromethyl-ethyl]-phenol (example 2) and 3-bromo-1-propanol was prepared 3-{2-methyl-4-[2,2,2-trifluoro-1-(4-methoxy-benzyloxy)-1-trifluoromethyl-ethyl]-phenoxy}-propan-1-ol as white solid, MS: 452 (M)$^+$.

18.2

In analogy to example 8.2-8.3, from 3-{2-methyl-4-[2,2,2-trifluoro-1-(4-methoxy-benzyloxy)-1-trifluoromethyl-ethyl]-phenoxy}-propan-1-ol and (4-hydroxy-phenyl)-acetic acid methyl ester was prepared (4-{3-[2-methyl-4-(2,2,2-trifluoro-1-hydroxy-1-trifluoromethyl-ethyl)-phenoxy]-propoxy}-phenyl)-acetic acid methyl ester as a yellow oil, MS: 479 (M−H)$^-$.

Example 19

4-{3-[2-Methyl-4-(2,2,2-trifluoro-1-hydroxy-1-trifluoromethyl-ethyl)-phenoxy]-propoxy}-benzoic acid methyl ester In analogy to example 8.2-8.3, from 3-{2-methyl-4-[2,2,2-trifluoro-1-(4-methoxy-benzyloxy)-1-trifluoromethyl-ethyl]-phenoxy}-propan-1-ol and 4-hydroxy-benzoic acid methyl ester was prepared 4-{3-[2-methyl-4-(2,2,2-trifluoro-1-hydroxy-1-trifluoromethyl-ethyl)-phenoxy]-propoxy}-benzoic acid methyl ester as a white solid, MS: 465 (M−H)$^-$.

Example 20

3-(4-{3-[2-Chloro-4-(2,2,2-trifluoro-1-hydroxy-1-trifluoromethyl-ethyl)-phenoxy]-propoxy}-phenyl)-propionic acid methyl ester 20.1

In analogy to example 8.1, from 2-chloro-4-[2,2,2-trifluoro-1-(4-methoxy-benzyloxy)-1-trifluoromethyl-ethyl]-phenol (example 3) and 3-bromo-1-propanol was prepared 3-{2-chloro-4-[2,2,2-trifluoro-1-(4-methoxy-benzyloxy)-1-trifluoromethyl-ethyl]-phenoxy}-propan-1-ol as a yellow oil, MS: 472 (M, 1Cl)$^+$.

20.2

In analogy to example 8.2-8.3, from 3-{2-chloro-4-[2,2,2-trifluoro-1-(4-methoxy-benzyloxy)-1-trifluoromethyl-ethyl]-phenoxy}-propan-1-ol and 3-(4-hydroxy-phenyl)-propionic acid methyl ester was prepared 3-(4-{3-[2-chloro-4-(2,2,2-trifluoro-1-hydroxy-1-trifluoromethyl-ethyl)-phenoxy]-propoxy}-phenyl)-propionic acid methyl ester as a colorless oil, MS: 513 (M−H, 1Cl)$^-$.

Example 21

(4-{3-[2-Chloro-4-(2,2,2-trifluoro-1-hydroxy-1-trifluoromethyl-ethyl)-phenoxy]-propoxy}-phenyl)-acetic acid methyl ester In analogy to example 8.2-8.3, from 3-{2-chloro-4-[2,2,2-trifluoro-1-(4-methoxy-benzyloxy)-1-trifluoromethyl-ethyl]-phenoxy}-propan-1-ol and (4-hydroxy-phenyl)-acetic acid methyl ester was prepared (4-{3-[2-chloro-4-(2,2,2-trifluoro-1-hydroxy-1-trifluoromethyl-ethyl)-phenoxy]-propoxy}-phenyl)-acetic acid methyl ester as a colorless oil, MS: 499 (M−H, 1Cl)$^-$.

Example 22

4-{3-[2-Chloro-4-(2,2,2-trifluoro-1-hydroxy-1-trifluoromethyl-ethyl)-phenoxy]-propoxy}-benzoic acid methyl ester In analogy to example 8.2-8.3, from 3-{2-chloro-4-[2,2,2-trifluoro-1-(4-methoxy-benzyloxy)-1-trifluoromethyl-ethyl]-phenoxy}-propan-1-ol and 4-hydroxy-benzoic acid methyl ester was prepared 4-{3-[2-chloro-4-(2,2,2-trifluoro-1-hydroxy-1-trifluoromethyl-ethyl)-phenoxy]-propoxy}-benzoic acid methyl ester as a white solid, MS: 485 (M−H, 1Cl)$^-$.

Example 23

(4-{3-[2,6-Dimethyl-4-(2,2,2-trifluoro-1-hydroxy-1-trifluoromethyl-ethyl)-phenoxy]-propoxy}-phenyl)-acetic acid methyl ester 23.1

In analogy to example 8.1, from 2,6-dimethyl-4-[2,2,2-trifluoro-1-(4-methoxy-benzyloxy)-1-trifluoromethyl-ethyl]-phenol (example 4) and 3-bromo-1-propanol was prepared 3-{2,6-dimethyl-4-[2,2,2-trifluoro-1-(4-methoxy-benzyloxy)-1-trifluoromethyl-ethyl]-phenoxy}-propan-1-ol as a yellow oil, MS: 466 (M)$^+$.

23.2

In analogy to example 8.2-8.3, from 3-{2,6-dimethyl-4-[2,2,2-trifluoro-1-(4-methoxy-benzyloxy)-1-trifluoromethyl-ethyl]-phenoxy}-propan-1-ol and (4-hydroxy-phenyl)-acetic acid methyl ester was prepared (4-{3-[2,6-dimethyl-4-(2,2,2-trifluoro-1-hydroxy-1-trifluoromethyl-ethyl)-phenoxy]-propoxy}-phenyl)-acetic acid methyl ester as a colorless oil, MS: 493 (M−H)$^-$.

Example 24

4-{3-[2,6-Dimethyl-4-(2,2,2-trifluoro-1-hydroxy-1-trifluoromethyl-ethyl)-phenoxy]-propoxy}-benzoic acid methyl ester In analogy to example 8.2-8.3, from 3-{2,6-dimethyl-4-[2,2,2-trifluoro-1-(4-methoxy-benzyloxy)-1-trifluoromethyl-ethyl]-phenoxy}-propan-1-ol and 4-hydroxy-benzoic acid methyl ester was prepared 4-{3-[2,6-dimethyl-4-(2,2,2-trifluoro-1-hydroxy-1-trifluoromethyl-ethyl)-phenoxy]-propoxy}-benzoic acid methyl ester as a colorless oil, MS: 479 (M−H)$^-$.

Example 25

4-{3-[2-Methyl-4-(2,2,2-trifluoro-1-hydroxy-1-trifluoromethyl-ethyl)-phenoxy]-propoxy}-benzoic acid 94 mg (0.2 mmol) of 4-{3-[2-methyl-4-(2,2,2-trifluoro-1-hydroxy-1-trifluoromethyl-ethyl)-phenoxy]-propoxy}-benzoic acid methyl ester (example 19) in 2 mL of THF were treated with 2 mL of 1M LiOH at room temperature overnight. 1M KHSO$_4$ solution was added, the phases were separated, and the inorganic one was extracted with EtOAc. The combined organic phases were washed with brine, dried (Na$_2$SO$_4$) and evaporated. The crude product was purified by column chromatography with CH$_2$Cl$_2$/MeOH 95:5 to give 60 mg (65%) 4-{3-[2-methyl-4-(2,2,2-trifluoro-1-hydroxy-1-trifluoromethyl-ethyl)-phenoxy]-propoxy}-benzoic acid as a light yellow solid, MS: 451 (M−H)$^-$.

Example 26

(4-{3-[2-Methyl-4-(2,2,2-trifluoro-1-hydroxy-1-trifluoromethyl-ethyl)-phenoxy]-propoxy}-phenyl)-acetic acid In analogy to example 25, from (4-{3-[2-methyl-4-(2,2,2-trifluoro-1-hydroxy-1-trifluoromethyl-ethyl)-phenoxy]-propoxy}-phenyl)-acetic acid methyl ester (example 18) was prepared (4-{3-[2-methyl-4-(2,2,2-trifluoro-1-hydroxy-1- trifluoromethyl-ethyl)-phenoxy]-propoxy}-phenyl)-acetic acid as a colorless oil, MS: 435 (M–H)⁻.

Example 27

(4-{3-[2,6-Dimethyl-4-(2,2,2-trifluoro-1-hydroxy-1-trifluoromethyl-ethyl)-phenoxy]-propoxy}-phenyl)-acetic acid In analogy to example 25, from (4-{3-[2,6-dimethyl-4-(2,2,2-trifluoro-1-hydroxy-1-trifluoromethyl-ethyl)-phenoxy]-propoxy}-phenyl)-acetic acid methyl ester (example 23) was prepared (4-{3-[2,6-dimethyl-4-(2,2,2-trifluoro-1-hydroxy-1-trifluoromethyl-ethyl)-phenoxy]-propoxy}-phenyl)-acetic acid as a light brown oil, MS: 479 (M–H)⁻.

Example 28

4-{3-[2,6-Dimethyl-4-(2,2,2-trifluoro-1-hydroxy-1-trifluoromethyl-ethyl)-phenoxy]-propoxy}-benzoic acid In analogy to example 25, from 4-{3-[2,6-dimethyl-4-(2,2,2-trifluoro-1-hydroxy-1-trifluoromethyl-ethyl)-phenoxy]-propoxy}-benzoic acid methyl ester (example 24) was prepared 4-{3-[2,6-dimethyl-4-(2,2,2-trifluoro-1-hydroxy-1-trifluoromethyl-ethyl)-phenoxy]-propoxy}-benzoic acid as a white solid, MS: 465 (M–H)⁻.

Example 29

4-{2-[2,6-Dimethyl-4-(2,2,2-trifluoro-1-hydroxy-1-trifluoromethyl-ethyl)-phenoxy]-ethoxy}-benzoic acid methyl ester 29.1
In analogy to example 8.1, 2,6-dimethyl-4-[2,2,2-trifluoro-1-(4-methoxy-benzyloxy)-1-trifluoromethyl-ethyl]-phenol (example 4) and 2-bromo-ethanol was prepared 2-{2,6-dimethyl-4-[2,2,2-trifluoro-1-(4-methoxy-benzyloxy)-1-trifluoromethyl-ethyl]-phenoxy}-ethanol as a white solid, MS: 470 (M+NH₄)⁺.

29.2
In analogy to example 8.2, from 2-{2,6-dimethyl-4-[2,2,2-trifluoro-1-(4-methoxy-benzyloxy)-1-trifluoromethyl-ethyl]-phenoxy}-ethanol and 4-hydroxy-benzoic acid methyl ester was prepared 4-(2-{2,6-dimethyl-4-[2,2,2-trifluoro-1-(4-methoxy-benzyloxy)-1-trifluoromethyl-ethyl]-phenoxy}-ethoxy)-benzoic acid methyl ester as a colorless oil, MS: 604 (M+NH₄)⁺.

29.3
To 105 mg (0.2 mmol) of 4-(2-{2,6-dimethyl-4-[2,2,2-trifluoro-1-(4-methoxy-benzyloxy)-1-trifluoromethyl-ethyl]-phenoxy}-ethoxy)-benzoic acid methyl ester in 5 mL of dichloroethane 61 mg (0.3 mmol) of DDQ and a drop of water were added. The reaction mixture was stirred at 70° C. overnight, cooled to room temperature and was diluted with dichloromethane and EtOAc, dried (Na₂SO₄) and evaporated. Column chromatography on ISOLUTE Flash NH₂ with EtOAc/n-heptane 1:1 gave 21 mg (25%) of 4-{2-[2,6-dimethyl-4-(2,2,2-trifluoro-1-hydroxy-1-trifluoromethyl-ethyl)-phenoxy]-ethoxy}-benzoic acid methyl ester as a light yellow solid, MS: 465 (M–H)⁻.

Example 30

3-(4-{(S)-2-[2-Methyl-4-(2,2,2-trifluoro-1-hydroxy-1-trifluoromethyl-ethyl)-phenoxy]-3-phenyl-propoxy}-phenyl)-propionic acid methyl ester 30.1
To 1.27 g (4.9 mmol) of (R)-2-hydroxy-3-phenyl-propionic acid benzyl ester in 10 mL of THF were added 1.5 g (3.8 mmol) of 2-methyl-4-[2,2,2-trifluoro-1-(4-methoxy-benzyloxy)-1-trifluoromethyl-ethyl]-phenol (example 2) and 1.3 g (4.9 mmol) of triphenylphosphine. The mixture was cooled to 0° C., treated with 0.77 mL (4.9 mmol) of DEAD and stirred at room temperature overnight. The solvent was evaporated and the crude mixture was purified by column chromatography on silica gel with EtOAc/n-heptane 1:4 to yield 1.7 g (71%) of (S)-2-{2-methyl-4-[2,2,2-trifluoro-1-(4-methoxy-benzyloxy)-1-trifluoromethyl-ethyl]-phenoxy}-3-phenyl-propionic acid benzyl ester as a light yellow oil, MS: 632 (M)⁺.

30.2
1.7 g (2.7 mmol) of (S)-2-{2-methyl-4-[2,2,2-trifluoro-1-(4-methoxy-benzyloxy)-1-trifluoromethyl-ethyl]-phenoxy}-3-phenyl-propionic acid benzyl ester was dissolved in a mixture of 11 mL of methanol and 11 mL of THF and cooled to 0° C. To this solution 1.0 g (26.9 mmol) of NaBH₄ were added in portions, and the mixture was slowly warmed to room temperature overnight. Water was added, the phases were separated and the inorganic one was extracted with dichloromethane. The combined organic phases were washed with brine, dried (Na₂SO₄), filtered and evaporated. Purification by column chromatography with CH₂Cl₂/MeOH 95:5 yielded 960 mg (68%) (S)-2-{2-methyl-4-[2,2,2-trifluoro-1-(4-methoxy-benzyloxy)-1-trifluoromethyl-ethyl]-phenoxy}-3-phenyl-propan-1-ol as a light yellow oil, MS: 528 (M)⁺.

30.3
To 320 mg (0.6 mmol) of (S)-2-{2-methyl-4-[2,2,2-trifluoro-1-(4-methoxy-benzyloxy)-1-trifluoromethyl-ethyl]-phenoxy}-3-phenyl-propan-1-ol in 5 mL of THF were added 0.14 g (0.8 mmol) of 3-(4-hydroxy-phenyl)-propionic acid methyl ester and 0.2 g (0.8 mmol) of triphenylphosphine. The mixture was cooled to 0°, was treated with 0.12 mL (0.8 mmol) of DEAD and was stirred at room temperature overnight. A solution of NH₄Cl was added, the phases were separated and the inorganic one was extracted with EtOAc. The combined organic phases were washed with brine, dried (Na₂SO₄), filtered and evaporated. The crude product was purified by column chromatography on silica gel with EtOAc/n-heptane 1:3 to yield 330 mg (79%) of 3-[4-((S)-2-{2-methyl-4-[2,2,2-trifluoro-1-(4-methoxy-benzyloxy)-1-trifluoromethyl-ethyl]-phenoxy}-3-phenyl-propoxy)-phenyl]-propionic acid methyl ester as a yellow oil.

30.4
330 mg (0.5 mmol) of 3-[4-((S)-2-{2-methyl-4-[2,2,2-trifluoro-1-(4-methoxy-benzyloxy)-1-trifluoromethyl-ethyl]-phenoxy}-3-phenyl-propoxy)-phenyl]-propionic acid methyl ester in 10 mL of EtOAc were hydrogenated in the presence of 200 mg of 10% Pd/C. After removal of the catalyst and evaporation of the solvent, the residue was purified by column chromatography on silica gel with EtOAc/n-heptane 1:4 to yield 116 mg (42%) of 3-(4-{(S)-2-[2-methyl-4-(2,2,2-trifluoro-1-hydroxy-1-trifluoromethyl-ethyl)-phenoxy]-3-phenyl-propoxy}-phenyl)-propionic acid methyl ester as a light yellow oil, MS: 569 (M–H)⁻.

Example 31

(4-{(S)-2-[2-Methyl-4-(2,2,2-trifluoro-1-hydroxy-1-trifluoromethyl-ethyl)-phenoxy]-3-phenyl-propoxy}-phenyl)-acetic acid methyl ester In analogy to example 30.3-30.4, from (S)-2-{2-methyl-4-[2,2,2-trifluoro-1-(4-methoxy-benzyloxy)-1-trifluoromethyl-ethyl]-phenoxy}-3-phenyl-propan-1-ol and (4-hydroxy-phenyl)-acetic acid methyl ester was prepared (4-{(S)-2-[2-methyl-4-(2,2,2-trifluoro-1-hydroxy-1- trifluoromethyl-ethyl)-phenoxy]-3-phenyl-propoxy}-phenyl)-acetic acid methyl ester as a colorless oil, MS: 555 (M–H)⁻.

Example 32

4-{(S)-2-[2-Methyl-4-(2,2,2-trifluoro-1-hydroxy-1-trifluoromethyl-ethyl)-phenoxy]-3-phenyl-propoxy}-benzoic acid methyl ester In analogy to example 30.3-30.4, from (S)-2-{2-methyl-4-[2,2,2-trifluoro-1-(4-methoxy-benzyloxy)-1-trifluoromethyl-ethyl]-phenoxy}-3-phenyl-propan-1-ol and 4-hydroxy-benzoic acid methyl ester was prepared 4-{(S)-2-[2-methyl-4-(2,2,2-trifluoro-1-hydroxy-1-trifluoromethyl-ethyl)-phenoxy]-3-phenyl-propoxy}-benzoic acid methyl ester as a light yellow oil, MS: 541 (M–H)⁻.

Example 33

(4-{(S)-3-Phenyl-2-[4-(2,2,2-trifluoro-1-hydroxy-1-trifluoromethyl-ethyl)-phenoxy]-propoxy}-phenyl)-acetic acid methyl ester 33.1
In analogy to example 30.1-30.2, from (R)-2-hydroxy-3-phenyl-propionic acid benzyl ester and 4-[2,2,2-trifluoro-1-(4-methoxy-benzyloxy)-1-trifluoromethyl-ethyl]-phenol (example 1) was prepared (S)-3-phenyl-2-{4-[2,2,2-trifluoro-1-(4-methoxy-benzyloxy)-1-trifluoromethyl-ethyl]-phenoxy}-propan-1-ol as a light yellow oil, MS: 514 (M)⁺.

33.2
In analogy to example 30.3-30.4, from (S)-3-phenyl-2-{4-[2,2,2-trifluoro-1-(4-methoxy-benzyloxy)-1-trifluoromethyl-ethyl]-phenoxy}-propan-1-ol and (4-hydroxy-phenyl)-acetic acid methyl ester was prepared (4-{(S)-3-phenyl-2-[4-(2,2,2-trifluoro-1-hydroxy-1-trifluoromethyl-ethyl)-phenoxy]-propoxy}-phenyl)-acetic acid methyl ester as a colorless oil, MS: 541 (M–H)⁻.

Example 34

4-{(S)-3-Phenyl-2-[4-(2,2,2-trifluoro-1-hydroxy-1-trifluoromethyl-ethyl)-phenoxy]-propoxy}-benzoic acid methyl ester In analogy to example 30.3-30.4, from (S)-3-phenyl-2-{4-[2,2,2-trifluoro-1-(4-methoxy-benzyloxy)-1-trifluoromethyl-ethyl]-phenoxy}-propan-1-ol and 4-hydroxy-benzoic acid methyl ester was prepared 4-{(S)-3-phenyl-2-[4-(2,2,2-trifluoro-1-hydroxy-1-trifluoromethyl-ethyl)-phenoxy]-propoxy}-benzoic acid methyl ester as a colorless oil, MS: 527 (M–H)⁻.

Example 35

(4-{(S)-2-[2-Methyl-4-(2,2,2-trifluoro-1-hydroxy-1-trifluoromethyl-ethyl)-phenoxy]-3-phenyl-propoxy}-phenyl)-acetic acid In analogy to example 25, from (4-{(S)-2-[2-methyl-4-(2,2,2-trifluoro-1-hydroxy-1-trifluoromethyl-ethyl)-phenoxy]-3-phenyl-propoxy}-phenyl)-acetic acid methyl ester (example 31) was prepared (4-{(S)-2-[2-methyl-4-(2,2,2-trifluoro-1-hydroxy-1-trifluoromethyl-ethyl)-phenoxy]-3-phenyl-propoxy}-phenyl)-acetic acid as a colorless oil, MS: 541 (M–H)⁻.

Example 36

4-{(S)-2-[2-Methyl-4-(2,2,2-trifluoro-1-hydroxy-1-trifluoromethyl-ethyl)-phenoxy]-3-phenyl-propoxy}-benzoic acid In analogy to example 25, from 4-{(S)-2-[2-methyl-4-(2,2,2-trifluoro-1-hydroxy-1-trifluoromethyl-ethyl)-phenoxy]-3-phenyl-propoxy}-benzoic acid methyl ester (example 32) was prepared 4-{(S)-2-[2-methyl-4-(2,2,2-trifluoro-1-hydroxy-1-trifluoromethyl-ethyl)-phenoxy]-3-phenyl-propoxy}-benzoic acid as a colorless oil, MS: 527 (M–H)⁻.

Example 37

(4-{(S)-3-Phenyl-2-[4-(2,2,2-trifluoro-1-hydroxy-1-trifluoromethyl-ethyl)-phenoxy]-propoxy}-phenyl)-acetic acid In analogy to example 25, from (4-{(S)-3-phenyl-2-[4-(2,2,2-trifluoro-1-hydroxy-1-trifluoromethyl-ethyl)-phenoxy]-propoxy}-phenyl)-acetic acid methyl ester (example 33) was prepared (4-{(S)-3-phenyl-2-[4-(2,2,2-trifluoro-1-hydroxy-1-trifluoromethyl-ethyl)-phenoxy]-propoxy}-phenyl)-acetic acid as a colorless oil, MS: 527 (M–H)⁻.

Example 38

4-{(S)-3-Phenyl-2-[4-(2,2,2-trifluoro-1-hydroxy-1-trifluoromethyl-ethyl)-phenoxy]-propoxy}-benzoic acid In analogy to example 25, from 4-{(S)-3-phenyl-2-[4-(2,2,2-trifluoro-1-hydroxy-1-trifluoromethyl-ethyl)-phenoxy]-propoxy}-benzoic acid methyl ester (example 34) was prepared 4-{(S)-3-phenyl-2-[4-(2,2,2-trifluoro-1-hydroxy-1-trifluoromethyl-ethyl)-phenoxy]-propoxy}-benzoic acid as a colorless oil, MS: 513 (M–H)⁻.

Example 39

Rac 1,1,1,3,3,3-Hexafluoro-2-{4-[2-(4-hydroxymethyl-phenoxy)-1-phenyl-ethoxy]-phenyl}-propan-2-ol 39.1
In analogy to example 9.1, from rac 2-phenyl-oxirane and p-cresol was prepared rac 1-phenyl-2-p-tolyloxy-ethanol, MS: 228 (M)⁺, and rac 2-phenyl-2-p-tolyloxy-ethanol, MS: 228 (M)⁺.

39.2
In analogy to example 9.2, from 4-[2,2,2-trifluoro-1-(4-methoxy-benzyloxy)-1-trifluoromethyl-ethyl]-phenol (example 1) and rac 1-phenyl-2-p-tolyloxy-ethanol was prepared rac 1-(1-phenyl-2-p-tolyloxy-ethoxy)-4-[2,2,2-trifluoro-1-(4-methoxy-benzyloxy)-1-trifluoromethyl-ethyl]-benzene as yellow oil, MS: 590 (M)⁺.

39.3
90 mg (0.15 mmol) of rac 1-(1-phenyl-2-p-tolyloxy-ethoxy)-4-[2,2,2-trifluoro-1-(4-methoxy-benzyloxy)-1-trifluoromethyl-ethyl]-benzene in 3 ml of a mixture of acetonitrile:water (9:1) were treated with 100 mg (0.18 mmol) of ceric ammonium nitrate at room temperature overnight. An additional 100 mg (0.18 mmol) of ceric ammonium nitrate were added and stirring was continued. EtOAc and 1M KHSO$_4$ were added and the phases were separated. The inorganic one was extracted with EtOAC, the combined organic phases were washed with brine, dried (Na$_2$SO$_4$) and evaporated. Column chromatography on silica gel gave 44 mg (48%) of rac 4-(2-phenyl-2-{4-[2,2,2-trifluoro-1-(4-methoxy-benzyloxy)-1-trifluoromethyl-ethyl]-phenoxy}-ethoxy)-benzaldehyde, MS: 663 (M+OAc)$^-$.

39.4

To 44 mg (0.07 mmol) of rac 4-(2-phenyl-2-{4-[2,2,2-trifluoro-1-(4-methoxy-benzyloxy)-1-trifluoromethyl-ethyl]-phenoxy}-ethoxy)-benzaldehyde in 2 mL of dichloroethane 33 mg (0.15 mmol) of DDQ and a drop of water were added. The reaction mixture was stirred at 70° C. overnight, cooled to room temperature and was diluted with dichloromethane and EtOAc, dried (Na$_2$SO$_4$), filtered and evaporated. Column chromatography on silica gel with EtOAc/n-heptane 1:5 gave 22 mg (62%) of rac 4-{2-phenyl-2-[4-(2,2,2-trifluoro-1-hydroxy-1-trifluoromethyl-ethyl)-phenoxy]-ethoxy}-benzaldehyde, MS: 483 (M–H)$^-$.

39.5

40 mg (0.08 mmol) of rac 4-{2-phenyl-2-[4-(2,2,2-trifluoro-1-hydroxy-1-trifluoromethyl-ethyl)-phenoxy]-ethoxy}-benzaldehyde in 2 mL of a mixture of THF/EtOH (1:1) were treated with 31 mg (0.8 mmol) of NaBH$_4$ at 0° C. The mixture was stirred at room temperature, water and EtOAc were added, and the phases were separated. The inorganic phase was extracted with EtOAc, and the combined organic ones were washed with brine, dried (Na$_2$SO$_4$), filtered and evaporated. Column chromatography on ISOLUTE Flash NH$_2$ with EtOAc yielded 24 mg (59%) of rac 1,1,1,3,3,3-hexafluoro-2-{4-[2-(4-hydroxymethyl-phenoxy)-1-phenyl-ethoxy]-phenyl}-propan-2-ol as a colorless oil, MS: 485 (M–H)$^-$.

Example 40

1,1,1,3,3,3-Hexafluoro-2-(3-methyl-4-phenethyloxy-phenyl)-propan-2-ol

In analogy to example 13.1 and 29.3, from 2-methyl-4-[2,2,2-trifluoro-1-(4-methoxy-benzyloxy)-1-trifluoromethyl-ethyl]-phenol (example 2) and phenethyl bromide was prepared 1,1,1,3,3,3-hexafluoro-2-(3-methyl-4-phenethyloxy-phenyl)-propan-2-ol as a light yellow oil, MS: 377 (M–H)$^-$.

Example 41

Rac 1,1,1,3,3,3-Hexafluoro-2-[3-methyl-4-(1-phenyl-ethoxy)-phenyl]-propan-2-ol

In analogy to example 13.1 and 29.3, from 2-methyl-4-[2,2,2-trifluoro-1-(4-methoxy-benzyloxy)-1-trifluoromethyl-ethyl]-phenol (example 2) and rac (1-bromo-ethyl)-benzene was prepared rac 1,1,1,3,3,3-hexafluoro-2-[3-methyl-4-(1-phenyl-ethoxy)-phenyl]-propan-2-ol as a colorless oil, MS: 377 (M–H)$^-$.

Example 42

2-{4-[2-(3-Chloro-phenyl)-5-methyl-oxazol-4-ylmethoxy]-phenyl}-1,1,1,3,3,3-hexafluoro-propan-2-ol In analogy to example 13.1 and 29.3, from 4-[2,2,2-trifluoro-1-(4-methoxy-benzyloxy)-1-trifluoromethyl-ethyl]-phenol (example 1) and 4-chloromethyl-2-(3-chloro-phenyl)-5-methyl-oxazole (CAS 475481-97-1, prepared according to WO2002092084) was prepared 2-{4-[2-(3-chloro-phenyl)-5-methyl-oxazol-4-ylmethoxy]-phenyl}-1,1,1,3,3,3-hexafluoro-propan-2-ol as a white solid, MS: 464 (M–H, 1Cl)$^-$.

Example 43

2-[4-(3,5-Dimethyl-isoxazol-4-ylmethoxy)-phenyl]-1,1,1,3,3,3-hexafluoro-propan-2-ol In analogy to example 13.1 and 29.3, from 4-[2,2,2-trifluoro-1-(4-methoxy-benzyloxy)-1-trifluoromethyl-ethyl]-phenol (example 1) and 4-chloromethyl-3,5-dimethyl-isoxazole (CAS 19788-37-5) was prepared 2-[4-(3,5-dimethyl-isoxazol-4-ylmethoxy)-phenyl]-1,1,1,3,3,3-hexafluoro-propan-2-ol as a white solid, MS: 368 (M–H)$^-$.

Example 44

1,1,1,3,3,3-Hexafluoro-2-[4-(5-methyl-isoxazol-3-ylmethoxy)-phenyl]-propan-2-ol

In analogy to example 13.1 and 29.3, from 4-[2,2,2-trifluoro-1-(4-methoxy-benzyloxy)-1-trifluoromethyl-ethyl]-phenol (example 1) and 3-chloromethyl-5-methyl-isoxazole (CAS 35166-37-1) was prepared 1,1,1,3,3,3-hexafluoro-2-[4-(5-methyl-isoxazol-3-ylmethoxy)-phenyl]-propan-2-ol as a white solid, MS: 354 (M–H)$^-$.

Example 45

1,1,1,3,3,3-Hexafluoro-2-[4-(5-methyl-2-phenyl-2H-[1,2,3]triazol-4-ylmethoxy)-phenyl]-propan-2-ol In analogy to example 13.1 and 29.3, from 4-[2,2,2-trifluoro-1-(4-methoxy-benzyloxy)-1-trifluoromethyl-ethyl]-phenol (example 1) and 4-bromomethyl-5-methyl-2-phenyl-2H-[1,2,3]triazole (CAS 13322-02-6) was prepared 1,1,1,3,3,3-hexafluoro-2-[4-(5-methyl-2-phenyl-2H-[1,2,3]triazol-4-ylmethoxy)-phenyl]-propan-2-ol as a colorless oil, MS: 430 (M–H)$^-$.

Example 46

1,1,1,3,3,3-Hexafluoro-2-[4-(5-methyl-3-phenyl-isoxazol-4-ylmethoxy)-phenyl]-propan-2-ol In analogy to example 13.1 and 29.3, from 4-[2,2,2-trifluoro-1-(4-methoxy-benzyloxy)-1-trifluoromethyl-ethyl]-phenol (example 1) and 4-bromomethyl-5-methyl-3-phenyl-isoxazole (CAS 180597-83-5) was prepared 1,1,1,3,3,3-hexafluoro-2-[4-(5-methyl-3-phenyl-isoxazol-4-ylmethoxy)-phenyl]-propan-2-ol as a light yellow oil, MS: 430 (M–H)$^-$.

Example 47

3-[4-(2,2,2-Trifluoro-1-hydroxy-1-trifluoromethyl-ethyl)-phenoxymethyl]-benzoic acid methyl ester In analogy to example 13.1 and 29.3, from 4-[2,2,2-trifluoro-1-(4-methoxy-benzyloxy)-1-trifluoromethyl-ethyl]-phenol (example 1) and 3-bromomethyl-benzoic acid methyl ester (CAS 1129-28-8) was prepared 3-[4-(2,2,2-trifluoro-1-hydroxy-1-trifluoromethyl-ethyl)-phenoxymethyl]-benzoic acid methyl ester as a white solid, MS: 407 (M–H)$^-$.

Example 48

Lithium 4-{(S)-2-[2-methyl-4-(2,2,2-trifluoro-1-hydroxy-1-trifluoromethyl-ethyl)-phenoxy]-3-phenyl-propoxy}-benzoate 20.2 mg (0.04 mmol) of 4-{(S)-2-[2-methyl-4-(2,2,2-trifluoro-1-hydroxy-1-trifluoromethyl-ethyl)-phenoxy]-3-phenyl-propoxy}-benzoic acid (example 36) in 3 mL of THF were treated with 1 mg (0.04 mmol) of lithium hydroxide. The solvent was evaporated to give 21 mg (quantitative) of lithium 4-{(S)-2-[2-methyl-4-(2,2,2-trifluoro-1-hydroxy-1-trifluoromethyl-ethyl)-phenoxy]-3-phenyl-propoxy}-benzoate as a light yellow oil, MS: 527 (M–H)$^-$.

Example 49

Lithium (4-{(S)-3-phenyl-2-[4-(2,2,2-trifluoro-1-hydroxy-1-trifluoromethyl-ethyl)-phenoxy]-propoxy}-phenyl)-acetate In analogy to example 48, from (4-{(S)-3-phenyl-2-[4-(2,2,2-trifluoro-1-hydroxy-1-trifluoromethyl-ethyl)-phenoxy]-propoxy}-phenyl)-acetic acid (example 37) was prepared lithium (4-{(S)-3-phenyl-2-[4-(2,2,2-trifluoro-1-hydroxy-1-trifluoromethyl-ethyl)-phenoxy]-propoxy}-phenyl)-acetate as a light yellow oil, MS: 527 (M–H)$^-$.

Example 50

3-(4-{(R)-3-Phenyl-2-[4-(2,2,2-trifluoro-1-hydroxy-1-trifluoromethyl-ethyl)-phenoxy]-propoxy}-phenyl)-propionic acid methyl ester 50.1
In analogy to example 30.1, from (S)-2-hydroxy-3-phenyl-propionic acid methyl ester and 4-[2,2,2-trifluoro-1-(4-methoxy-benzyloxy)-1-trifluoromethyl-ethyl]-phenol (example 1) was prepared (R)-3-phenyl-2-{4-[2,2,2-trifluoro-1-(4-methoxy-benzyloxy)-1-trifluoromethyl-ethyl]-phenoxy}-propionic acid methyl ester as a yellow oil, MS: 676 (M)$^+$.

50.2
In analogy to example 30.2, from (R)-3-phenyl-2-{4-[2,2,2-trifluoro-1-(4-methoxy-benzyloxy)-1-trifluoromethyl-ethyl]-phenoxy}-propionic acid methyl ester was prepared (R)-3-phenyl-2-{4-[2,2,2-trifluoro-1-(4-methoxy-benzyloxy)-1-trifluoromethyl-ethyl]-phenoxy}-propan-1-ol as a light yellow oil, MS: 514 (M)$^+$.

50.3
In analogy to example 30.3 and 30.4, from (R)-3-phenyl-2-{4-[2,2,2-trifluoro-1-(4-methoxy-benzyloxy)-1-trifluoromethyl-ethyl]-phenoxy}-propan-1-ol and 3-(4-hydroxy-phenyl)-propionic acid methyl ester was prepared 3-(4-{(R)-3-phenyl-2-[4-(2,2,2-trifluoro-1-hydroxy-1-trifluoromethyl-ethyl)-phenoxy]-propoxy}-phenyl)-propionic acid methyl ester as a colorless oil, MS: 555 (M–H)$^-$.

Example 51

(4-{(R)-3-Phenyl-2-[4-(2,2,2-trifluoro-1-hydroxy-1-trifluoromethyl-ethyl)-phenoxy]-propoxy}-phenyl)-acetic acid methyl ester In analogy to examples 30.3 and 30.4, from (R)-3-phenyl-2-{4-[2,2,2-trifluoro-1-(4-methoxy-benzyloxy)-1-trifluoromethyl-ethyl]-phenoxy}-propan-1-ol and (4-hydroxy-phenyl)-acetic acid methyl ester was prepared (4-{(R)-3-phenyl-2-[4-(2,2,2-trifluoro-1-hydroxy-1-trifluoromethyl-ethyl)-phenoxy]-propoxy}-phenyl)-acetic acid methyl ester as a colorless oil, MS: 541 (M–H)$^-$.

Example 52

4-{(R)-3-Phenyl-2-[4-(2,2,2-trifluoro-1-hydroxy-1-trifluoromethyl-ethyl)-phenoxy]-propoxy}-benzoic acid methyl ester In analogy to examples 30.3 and 30.4, from (R)-3-phenyl-2-{4-[2,2,2-trifluoro-1-(4-methoxy-benzyloxy)-1-trifluoromethyl-ethyl]-phenoxy}-propan-1-ol and 4-hydroxy-benzoic acid methyl ester was prepared 4-{(R)-3-phenyl-2-[4-(2,2,2-trifluoro-1-hydroxy-1-trifluoromethyl-ethyl)-phenoxy]-propoxy}-benzoic acid methyl ester as a colorless oil, MS: 527 (M–H)$^-$.

Example 53

3-(4-{(R)-3-Phenyl-2-[4-(2,2,2-trifluoro-1-hydroxy-1-trifluoromethyl-ethyl)-phenoxy]-propoxy}-phenyl)-propionic acid In analogy to example 25, from 3-(4-{(R)-3-phenyl-2-[4-(2,2,2-trifluoro-1-hydroxy-1-trifluoromethyl-ethyl)-phenoxy]-propoxy}-phenyl)-propionic acid methyl ester (example 50) was prepared 3-(4-{(R)-3-phenyl-2-[4-(2,2,2-trifluoro-1-hydroxy-1-trifluoromethyl-ethyl)-phenoxy]-propoxy}-phenyl)-propionic acid as a colorless oil, MS: 541 (M–H)$^-$.

Example 54

(4-{(R)-3-Phenyl-2-[4-(2,2,2-trifluoro-1-hydroxy-1-trifluoromethyl-ethyl)-phenoxy]-propoxy}-phenyl)-acetic acid In analogy to example 25, from (4-{(R)-3-phenyl-2-[4-(2,2,2-trifluoro-1-hydroxy-1-trifluoromethyl-ethyl)-phenoxy]-propoxy}-phenyl)-acetic acid methyl ester (example 51) was prepared (4-{(R)-3-phenyl-2-[4-(2,2,2-trifluoro-1-hydroxy-1-trifluoromethyl-ethyl)-phenoxy]-propoxy}-phenyl)-acetic acid as a colorless oil, MS: 527 (M–H)$^-$.

Example 55

4-{(R)-3-Phenyl-2-[4-(2,2,2-trifluoro-1-hydroxy-1-trifluoromethyl-ethyl)-phenoxy]-propoxy}-benzoic acid In analogy to example 25, from 4-{(R)-3-phenyl-2-[4-(2,2,2-trifluoro-1-hydroxy-1-trifluoromethyl-ethyl)-phenoxy]-propoxy}-benzoic acid methyl ester (example 52) was prepared 4-{(R)-3-phenyl-2-[4-(2,2,2-trifluoro-1-hydroxy-1-trifluoromethyl-ethyl)-phenoxy]-propoxy}-benzoic acid as a colorless oil, MS: 514 (M–H)$^-$.

Example 56

2-{4-[2-(3-Chloro-phenyl)-5-methyl-oxazol-4-ylmethoxy]-3-methyl-phenyl}-1,1,1,3,3,3-hexafluoro-propan-2-ol In analogy to examples 13.1 and 29.3, from 2-methyl-4-[2,2,2-trifluoro-1-(4-methoxy-benzyloxy)-1-trifluoromethyl-ethyl]-phenol (example 2) and 4-chloromethyl-2-(3-chloro-phenyl)-5-methyl-oxazole (CAS 475481-97-1, prepared according to WO2002092084) was prepared 2-{4-[2-(3-chloro-phenyl)-5-methyl-oxazol-4-ylmethoxy]-3-methyl-phenyl}-1,1,1,3,3,3-hexafluoro-propan-2-ol as a light yellow solid, MS: 478 (M–H, 1Cl)⁻.

Example 57

2-{3-Chloro-4-[2-(3-chloro-phenyl)-5-methyl-oxazol-4-ylmethoxy]-phenyl}-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-2-(3-chloro-phenyl)-5-methyl-oxazole (CAS 475481-97-1, prepared according to WO2002092084) was prepared 2-{3-chloro-4-[2-(3-chloro-phenyl)-5-methyl-oxazol-4-ylmethoxy]-phenyl}-1,1,1,3,3,3-hexafluoro-propan-2-ol as a white solid, MS: 498 (M–H, 2Cl)⁻.

Example 58

1,1,1,3,3,3-Hexafluoro-2-(4-phenethyloxy-phenyl)-propan-2-ol

In analogy to examples 13.1 and 29.3, from 4-[2,2,2-trifluoro-1-(4-methoxy-benzyloxy)-1-trifluoromethyl-ethyl]-phenol (example 1) and phenethyl bromide was prepared 1,1,1,3,3,3-hexafluoro-2-(4-phenethyloxy-phenyl)-propan-2-ol as a light yellow oil, MS: 362 (M–H)⁻.

Example 59

2-(3,5-Dimethyl-4-phenethyloxy-phenyl)-1,1,1,3,3,3-hexafluoro-propan-2-ol

In analogy to examples 13.1 and 29.3, from 2,6-dimethyl-4-[2,2,2-trifluoro-1-(4-methoxy-benzyloxy)-1-trifluoromethyl-ethyl]-phenol (example 4) and phenethyl bromide was prepared 2-(3,5-dimethyl-4-phenethyloxy-phenyl)-1,1,1,3,3,3-hexafluoro-propan-2-ol as a light yellow oil, MS: 391 (M–H)⁻.

Example 60

2-(3-Chloro-4-phenethyloxy-phenyl)-1,1,1,3,3,3-hexafluoro-propan-2-ol

In analogy to examples 13.1 and 29.3, from 2-chloro-4-[2,2,2-trifluoro-1-(4-methoxy-benzyloxy)-1-trifluoromethyl-ethyl]-phenol (example 3) and phenethyl bromide was prepared 2-(3-chloro-4-phenethyloxy-phenyl)-1,1,1,3,3,3-hexafluoro-propan-2-ol as a light yellow oil, MS: 397 (M–H, 1Cl)⁻.

Example 61

Rac 1,1,1,3,3,3-Hexafluoro-2-[4-(1-phenyl-ethoxy)-phenyl]-propan-2-ol

In analogy to examples 13.1 and 29.3, from 4-[2,2,2-trifluoro-1-(4-methoxy-benzyloxy)-1-trifluoromethyl-ethyl]-phenol (example 1) and rac (1-bromo-ethyl)-benzene was prepared rac 1,1,1,3,3,3-hexafluoro-2-[4-(1-phenyl-ethoxy)-phenyl]-propan-2-ol as a light yellow oil, MS: 363 (M–H)⁻.

Example 62

1,1,1,3,3,3-Hexafluoro-2-[3-methyl-4-(5-methyl-2-m-tolyl-oxazol-4-ylmethoxy)-phenyl]-propan-2-ol In analogy to examples 13.1 and 29.3, from 2-methyl-4-[2,2,2-trifluoro-1-(4-methoxy-benzyloxy)-1-trifluoromethyl-ethyl]-phenol (example 2) and 4-chloromethyl-5-methyl-2-m-tolyl-oxazole (CAS 521266-92-2, prepared according to WO2003037327) was prepared 1,1,1,3,3,3-hexafluoro-2-[3-methyl-4-(5-methyl-2-m-tolyl-oxazol-4-ylmethoxy)-phenyl]-propan-2-ol as a white solid, MS: 458 (M–H)⁻.

Example 63

2-{4-[2-(2-Chloro-phenyl)-5-methyl-oxazol-4-ylmethoxy]-3-methyl-phenyl}-1,1,1,3,3,3-hexafluoro-propan-2-ol In analogy to examples 13.1 and 29.3, from 2-methyl-4-[2,2,2-trifluoro-1-(4-methoxy-benzyloxy)-1-trifluoromethyl-ethyl]-phenol (example 2) and 4-chloromethyl-2-(2-chloro-phenyl)-5-methyl-oxazole (CAS 475481-96-0, prepared according to WO2002092084) was prepared 2-{4-[2-(2-chloro-phenyl)-5-methyl-oxazol-4-ylmethoxy]-3-methyl-phenyl}-1,1,1,3,3,3-hexafluoro-propan-2-ol as a white solid, MS: 478 (M–H, 1Cl)⁻.

Example 64

1,1,1,3,3,3-Hexafluoro-2-[3-methyl-4-(5-methyl-2-o-tolyl-oxazol-4-ylmethoxy)-phenyl]-propan-2-ol In analogy to examples 13.1 and 29.3, from 2-methyl-4-[2,2,2-trifluoro-1-(4-methoxy-benzyloxy)-1-trifluoromethyl-ethyl]-phenol (example 2) and 4-chloromethyl-5-methyl-2-o-tolyl-oxazole (CAS 671215-81-9, prepared according to WO2004031162) was prepared 1,1,1,3,3,3-hexafluoro-2-[3-methyl-4-(5-methyl-2-o-tolyl-oxazol-4-ylmethoxy)-phenyl]-propan-2-ol as a white solid, MS: 458 (M–H)⁻.

Example 65

1,1,1,3,3,3-Hexafluoro-2-{3-methyl-4-[5-methyl-2-(3-trifluoromethyl-phenyl)-oxazol-4-ylmethoxy]-phenyl}-propan-2-ol In analogy to examples 13.1 and 29.3, from 2-methyl-4-[2,2,2-trifluoro-1-(4-methoxy-benzyloxy)-1-trifluoromethyl-ethyl]-phenol (example 2) and 4-chloromethyl-5-methyl-2-(3-trifluoromethyl-phenyl)-oxazole (CAS 678164-78-8, prepared according to WO2004031162) was prepared 1,1,1,3,3,3-hexafluoro-2-{3-methyl-4-[5-methyl-2-(3-trifluoromethyl-phenyl)-oxazol-4-ylmethoxy]-phenyl}-propan-2-ol as a white solid, MS: 512 (M–H)⁻.

Example 66

1,1,1,3,3,3-Hexafluoro-2-{4-[2-(4-fluoro-3-methyl-phenyl)-5-methyl-oxazol-4-ylmethoxy]-3-methyl-phenyl}-propan-2-ol In analogy to examples 13.1 and 29.3, from 2-methyl-4-[2,2,2-trifluoro-1-(4-methoxy-benzyloxy)-1-trifluoromethyl-ethyl]-phenol (example 2) and 4-chloromethyl-2-(4-fluoro-3-methyl-phenyl)-5-methyl-oxazole (CAS 475481-98-2, prepared according to WO2002092084) was prepared 1,1,1,3,3,3-hexafluoro-2-{4-[2-(4-fluoro-3-methyl-phenyl)-5-methyl-oxazol-4-ylmethoxy]-3-methyl-phenyl}-propan-2-ol as a white solid, MS: 476 (M–H)⁻.

Example 67

2-{3-Chloro-4-[5-methyl-2-(4-trifluoromethyl-phenyl)-oxazol-4-ylmethoxy]-phenyl}-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-5-methyl-2-(4-trifluoromethyl-phenyl)-oxazole (CAS 174258-39-0, prepared according to WO2002092084) was prepared 2-{3- chloro-4-[5-methyl-2-(4-trifluoromethyl-phenyl)-oxazol-4-ylmethoxy]-phenyl}-1,1,1,3,3,3-hexafluoro-propan-2-ol as a white solid, MS: 532 (M–H, 1Cl)⁻.

Example 68

2-[3-Chloro-4-(5-methyl-2-m-tolyl-oxazol-4-ylmethoxy)-phenyl]-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-5-methyl-2-m-tolyl-oxazole (CAS 521266-92-2, prepared according to WO2003037327) was prepared 2-[3-chloro-4-(5-methyl-2-m-tolyl-oxazol-4-ylmethoxy)-phenyl]-1,1,1,3,3,3-hexafluoro-propan-2-ol as a white solid, MS: 478 (M–H, 1Cl)⁻.

Example 69

2-{3-Chloro-4-[2-(2-chloro-phenyl)-5-methyl-oxazol-4-ylmethoxy]-phenyl}-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-2-(2-chloro-phenyl)-5-methyl-oxazole (CAS 475481-96-0, prepared according to WO2002092084) was prepared 2-{3-chloro-4-[2-(2-chloro-phenyl)-5-methyl-oxazol-4-ylmethoxy]-phenyl}-1,1,1,3,3,3-hexafluoro-propan-2-ol as a white solid, MS: 498 (M–H, 2Cl)⁻.

Example 70

2-[3-Chloro-4-(5-methyl-2-o-tolyl-oxazol-4-ylmethoxy)-phenyl]-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-5-methyl-2-o-tolyl-oxazole (CAS 671215-81-9, prepared according to WO2004031162) was prepared 2-[3-chloro-4-(5-methyl-2-o-tolyl-oxazol-4-ylmethoxy)-phenyl]-1,1,1,3,3,3-hexafluoro-propan-2-ol as a white solid, MS: 478 (M–H, 1Cl)⁻.

Example 71

2-{3-Chloro-4-[5-methyl-2-(3-trifluoromethyl-phenyl)-oxazol-4-ylmethoxy]-phenyl}-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-5-methyl-2-(3-trifluoromethyl-phenyl)-oxazole (CAS 678164-78-8, prepared according to WO2004031162) was prepared 2-{3-chloro-4-[5-methyl-2-(3-trifluoromethyl-phenyl)-oxazol-4-ylmethoxy]-phenyl}-1,1,1,3,3,3-hexafluoro-propan-2-ol as a white solid, MS: 532 (M–H, 1Cl)⁻.

Example 72

2-{3-Chloro-4-[2-(4-fluoro-3-methyl-phenyl)-5-methyl-oxazol-4-ylmethoxy]-phenyl}-1,1,1,3,3,3-hexafluoro-propan-2-ol In analogy to examples 13.1 and 29.3, from 2-chloro-4-[2,2,2-trifluoro-1-(4-methoxy-benzyloxy)-1-trifluoromethyl-ethyl]-phenol (example 3) and 4-chloromethyl-2-(4-fluoro-3-methyl-phenyl)-5-methyl-oxazole (CAS 475481-98-2, prepared according to WO2002092084) was prepared 2-{3-chloro-4-[2-(4-fluoro-3-methyl-phenyl)-5-methyl-oxazol-4-ylmethoxy]-phenyl}-1,1,1,3,3,3-hexafluoro-propan-2-ol as a white solid, MS: 496 (M–H, 1Cl)⁻.

Example 73

2-{3-[2-(3-Chloro-phenyl)-5-methyl-oxazol-4-ylmethoxy]-phenyl}-1,1,1,3,3,3-hexafluoro-propan-2-ol In analogy to examples 13.1 and 29.3, from 3-[2,2,2-trifluoro-1-(4-methoxy-benzyloxy)-1-trifluoromethyl-ethyl]-phenol (example 5) and 4-chloromethyl-5-methyl-2-(3-trifluoromethyl-phenyl)-oxazole (CAS 678164-78-8, prepared according to WO2004031162) was prepared 2-{3-[2-(3-chloro-phenyl)-5-methyl-oxazol-4-ylmethoxy]-phenyl}-1,1,1,3,3,3-hexafluoro-propan-2-ol as a light yellow solid, MS: 464 (M–H, 1Cl)⁻.

Example 74

1,1,1,3,3,3-Hexafluoro-2-[3-(5-methyl-2-o-tolyl-oxazol-4-ylmethoxy)-phenyl]-propan-2-ol In analogy to examples 13.1 and 29.3, from 3-[2,2,2-trifluoro-1-(4-methoxy-benzyloxy)-1-trifluoromethyl-ethyl]-phenol (example 5) and 4-chloromethyl-5-methyl-2-o-tolyl-oxazole (CAS 671215-81-9, prepared according to WO2004031162) was prepared 1,1,1,3,3,3-hexafluoro-2-[3-(5-methyl-2-o-tolyl-oxazol-4-ylmethoxy)-phenyl]-propan-2-ol as a yellow oil, MS: 444 (M–H)⁻.

Example 75

1,1,1,3,3,3-Hexafluoro-2-{3-[5-methyl-2-(3-trifluoromethyl-phenyl)-oxazol-4-ylmethoxy]-phenyl}-propan-2-ol In analogy to examples 13.1 and 29.3, from 3-[2,2,2-trifluoro-1-(4-methoxy-benzyloxy)-1-trifluoromethyl-ethyl]-phenol (example 5) and 4-chloromethyl-5-methyl-2-(3-trifluoromethyl-phenyl)-oxazole (CAS 678164-78-8, prepared according to WO2004031162) was prepared 1,1,1,3,3,3-hexafluoro-2-{3-[5-methyl-2-(3-trifluoromethyl-phenyl)-oxazol-4-ylmethoxy]-phenyl}-propan-2-ol as a white solid, MS: 498 (M–H)⁻.

Example 76

2-{3-[2-(2-Chloro-phenyl)-5-methyl-oxazol-4-ylmethoxy]-phenyl}-1,1,1,3,3,3-hexafluoro-propan-2-ol In analogy to examples 13.1 and 29.3, from 3-[2,2,2-trifluoro-1-(4-methoxy-benzyloxy)-1-trifluoromethyl-ethyl]-phenol (example 5) and 4-chloromethyl-2-(2-chloro-phenyl)-5-methyl-oxazole (CAS 475481-96-0, prepared according to WO2002092084) was prepared 2-{3-[2-(2-chloro-phenyl)-5-methyl-oxazol-4-ylmethoxy]-phenyl}-1,1,1,3,3,3-hexafluoro-propan-2-ol as an orange oil, MS: 464 (M–H, 1Cl)⁻.

Example 77

1,1,1,3,3,3-Hexafluoro-2-[3-(5-methyl-2-m-tolyl-oxazol-4-ylmethoxy)-phenyl]-propan-2-ol In analogy to examples 13.1 and 29.3, from 3-[2,2,2-trifluoro-1-(4-methoxy-benzyloxy)-1-trifluoromethyl-ethyl]-phenol (example 5) and 4-chloromethyl-2-m-tolyl-oxazole (CAS 521266-92-2, prepared according to WO2003037327) was prepared 1,1,1,3,3,3-hexafluoro-2-[3-(5-methyl-2-m-tolyl-oxazol-4-ylmethoxy)-phenyl]-propan-2-ol as a yellow solid, MS: 444 (M–H)⁻.

Example 78

3-{4-[2-Chloro-4-(2,2,2-trifluoro-1-hydroxy-1-trifluoromethyl-ethyl)-phenoxymethyl]-5-methyl-oxazol-2-yl}-benzoic acid methyl ester In analogy to examples 13.1 and 29.3, from 2-chloro-4-[2,2,2-trifluoro-1-(4-methoxy-benzyloxy)-1-trifluoromethyl-ethyl]-phenol (example 3) and 3-(4-chloromethyl-5-methyl-oxazol-2-yl)-benzoic acid methyl ester (CAS 675148-35-3) was prepared 3-{4-[2-chloro-4-(2,2,2-trifluoro-1-hydroxy-1-trifluoromethyl-ethyl)-phenoxymethyl]-5-methyl-oxazol-2-yl}-benzoic acid methyl ester as a light yellow solid, MS: 522 (M−H, 1Cl)⁻.

Example 79

2-{3-Chloro-4-[2-(3-hydroxymethyl-phenyl)-5-methyl-oxazol-4-ylmethoxy]-phenyl}-1,1,1,3,3,3-hexafluoro-propan-2-ol In analogy to example 30.2, from 3-{4-[2-chloro-4-(2,2,2-trifluoro-1-hydroxy-1-trifluoromethyl-ethyl)-phenoxymethyl]-5-methyl-oxazol-2-yl}-benzoic acid methyl ester (example 78) was prepared 2-{3-chloro-4-[2-(3-hydroxymethyl-phenyl)-5-methyl-oxazol-4-ylmethoxy]-phenyl}-1,1,1,3,3,3-hexafluoro-propan-2-ol as a white solid, MS: 494 (M−H, 1 Cl)⁻.

Example 80

4-{5-Methyl-4-[3-(2,2,2-trifluoro-1-hydroxy-1-trifluoromethyl-ethyl)-phenoxymethyl]-oxazol-2-yl}-benzoic acid methyl ester In analogy to examples 13.1 and 29.3, from 3-[2,2,2-trifluoro-1-(4-methoxy-benzyloxy)-1-trifluoromethyl-ethyl]-phenol (example 5) and 4-(4-chloromethyl-5-methyl-oxazol-2-yl)-benzoic acid methyl ester (CAS 675148-38-6, WO2004024705) was prepared 4-{5-methyl-4-[3-(2,2,2-trifluoro-1-hydroxy-1-trifluoromethyl-ethyl)-phenoxymethyl]-oxazol-2-yl}-benzoic acid methyl ester as a light yellow solid, MS: 488 (M−H)⁻.

Example 81

4-{5-Methyl-4-[3-(2,2,2-trifluoro-1-hydroxy-1-trifluoromethyl-ethyl)-phenoxymethyl]-oxazol-2-yl}-benzoic acid In analogy to example 25, from 4-{5-methyl-4-[3-(2,2,2-trifluoro-1-hydroxy-1-trifluoromethyl-ethyl)-phenoxymethyl]-oxazol-2-yl}-benzoic acid methyl ester (example 80) was prepared 4-{5-methyl-4-[3-(2,2,2-trifluoro-1-hydroxy-1-trifluoromethyl-ethyl)-phenoxymethyl]-oxazol-2-yl}-benzoic acid as a white solid, MS: 474 (M−H)⁻.

Example 82

N,N-Dimethyl-4-{5-methyl-4-[3-(2,2,2-trifluoro-1-hydroxy-1-trifluoromethyl-ethyl)-phenoxymethyl]-oxazol-2-yl}-benzamide To 25 mg (0.05 mmol) of 4-{5-methyl-4-[3-(2,2,2-trifluoro-1-hydroxy-1-trifluoromethyl-ethyl)-phenoxymethyl]-oxazol-2-yl}-benzoic acid (example 81) in 1.5 ml of CH₂Cl₂ were added 8.6 mg (0.11 mol) of dimethylamine.HCl and 23 μl (0.11 mmol) of NMM. The solution was cooled to 0° C. and 13.1 mg (0.07 mmol, 1.3 eq) of EDCI and 1.4 mg (0.01 mmol) of HOBT were added. The mixture was stirred at room temperature overnight. Water was added and the inorganic phase was extracted with EtOAc. The organic phase was washed with brine, dried (Na₂SO₄), filtered and evaporated. Column chromatography with CH₂Cl₂/MeOH 98:2 gave 22 mg (83%) N,N-dimethyl-4-{5-methyl-4-[3-(2,2,2-trifluoro-1-hydroxy-1-trifluoromethyl-ethyl)-phenoxymethyl]-oxazol-2-yl}-benzamide as a colorless oil, MS: 501 (M−H)⁻.

Example 83

(3-{2-[4-(2,2,2-Trifluoro-1-hydroxy-1-trifluoromethyl-ethyl)-phenoxy]-ethoxy}-phenyl)-acetic acid methyl ester 83.1

In analogy to example 18.1, from 4-[2,2,2-trifluoro-1-(4-methoxy-benzyloxy)-1-trifluoromethyl-ethyl]-phenol (example 1) and 2-bromo-ethanol was prepared 2-{4-[2,2,2-trifluoro-1-(4-methoxy-benzyloxy)-1-trifluoromethyl-ethyl]-phenoxy}-ethanol as a white semisolid, MS: 424 (M)⁺.

83.2

In analogy to example 8.2-8.3, from 2-{4-[2,2,2-trifluoro-1-(4-methoxy-benzyloxy)-1-trifluoromethyl-ethyl]-phenoxy}-ethanol and (3-hydroxy-phenyl)-acetic acid methyl ester was prepared (3-{2-[4-(2,2,2-trifluoro-1-hydroxy-1-trifluoromethyl-ethyl)-phenoxy]-ethoxy}-phenyl)-acetic acid methyl ester as a white powder, MS: 451 (M−H)⁻.

Example 84

(4-{2-[4-(2,2,2-Trifluoro-1-hydroxy-1-trifluoromethyl-ethyl)-phenoxy]-ethoxy}-phenyl)-acetic acid methyl ester In analogy to example 8.2-8.3, from 2-{4-[2,2,2-trifluoro-1-(4-methoxy-benzyloxy)-1-trifluoromethyl-ethyl]-phenoxy}-ethanol (example 83.1) and (4-hydroxy-phenyl)-acetic acid methyl ester was prepared (4-{2-[4-(2,2,2-trifluoro-1-hydroxy-1-trifluoromethyl-ethyl)-phenoxy]-ethoxy}-phenyl)-acetic acid methyl ester as a white powder, MS: 451 (M−H)⁻.

Example 85

(3-{2-[3-(2,2,2-Trifluoro-1-hydroxy-1-trifluoromethyl-ethyl)-phenoxy]-ethoxy}-phenyl)-acetic acid methyl ester 85.1

In analogy to example 18.1, from 3-[2,2,2-trifluoro-1-(4-methoxy-benzyloxy)-1-trifluoromethyl-ethyl]-phenol (example 5) and 2-bromo-ethanol was prepared 2-{3-[2,2,2-trifluoro-1- (4-methoxy-benzyloxy)-1-trifluoromethyl-ethyl]-phenoxy}-ethanol as a colorless oil, MS: 424 (M)⁺.

85.2

In analogy to example 8.2-8.3, from 2-{3-[2,2,2-trifluoro-1-(4-methoxy-benzyloxy)-1-trifluoromethyl-ethyl]-phenoxy}-ethanol and (3-hydroxy-phenyl)-acetic acid methyl ester was prepared (3-{2-[3-(2,2,2-trifluoro-1-hydroxy-1-trifluoromethyl-ethyl)-phenoxy]-ethoxy}-phenyl)-acetic acid methyl ester as a white powder, MS: 451 (M−H)⁻.

Example 86

(3-{2-[4-(2,2,2-Trifluoro-1-hydroxy-1-trifluoromethyl-ethyl)-phenoxy]-ethoxy}-phenyl)-acetic acid In analogy to example 25, from (3-{2-[4-(2,2,2-trifluoro-1-hydroxy-1-trifluoromethyl-ethyl)-phenoxy]-ethoxy}-phenyl)-acetic acid methyl ester (example 83) was prepared (3-{2-[4-(2,2,2-trifluoro-1-hydroxy-1-trifluoromethyl-ethyl)-phenoxy]-ethoxy}-phenyl)-acetic acid as a white semisolid, MS: 437 (M−H)−.

Example 87

(4-{2-[4-(2,2,2-Trifluoro-1-hydroxy-1-trifluoromethyl-ethyl)-phenoxy]-ethoxy}-phenyl)-acetic acid In analogy to example 25, from (4-{2-[4-(2,2,2-trifluoro-1-hydroxy-1-trifluoromethyl-ethyl)-phenoxy]-ethoxy}-phenyl)-acetic acid methyl ester (example 84) was prepared (4-{2-[4-(2,2,2-trifluoro-1-hydroxy-1-trifluoromethyl-ethyl)-phenoxy]-ethoxy}-phenyl)-acetic acid as a colorless solid, MS: 437 (M−H)−.

Example 88 rac (3-{1-Phenyl-2-[3-(2,2,2-trifluoro-1-hydroxy-1-trifluoromethyl-ethyl)-phenoxy]-ethoxy}-phenyl)-acetic acid methyl ester In analogy to example 9.2, from rac 1-phenyl-2-{3-[2,2,2-trifluoro-1-(4-methoxy-benzyloxy)-1-trifluoromethyl-ethyl]-phenoxy}-ethanol (example 9.1) and (3-hydroxy-phenyl)-acetic acid methyl ester was prepared via rac [3-(1-phenyl-2-{3-[2,2,2-trifluoro-1-(4-methoxy-benzyloxy)-1-trifluoromethyl-ethyl]-phenoxy}-ethoxy)-phenyl]-acetic acid methyl ester, which was deprotected according to example 13.2, to give rac (3-{1-phenyl-2-[3-(2,2,2-trifluoro-1-hydroxy-1-trifluoromethyl-ethyl)-phenoxy]-ethoxy}-phenyl)-acetic acid methyl ester as a colorless oil, MS: 527 (M−H)−.

Example 89 rac-(3-{1-Phenyl-2-[3-(2,2,2-trifluoro-1-hydroxy-1-trifluoromethyl-ethyl)-phenoxy]-ethoxy}-phenyl)-acetic acid In analogy to example 25, from rac (3-{1-phenyl-2-[3-(2,2,2-trifluoro-1-hydroxy-1-trifluoromethyl-ethyl)-phenoxy]-ethoxy}-phenyl)-acetic acid methyl ester (example 88) was prepared rac-(3-{1-phenyl-2-[3-(2,2,2-trifluoro-1-hydroxy-1-trifluoromethyl-ethyl)-phenoxy]-ethoxy}-phenyl)-acetic acid as a colorless oil, MS: 513 (M−H)−.

Example 90 rac N,N-Dimethyl-2-(3-{1-phenyl-2-[3-(2,2,2-trifluoro-1-hydroxy-1-trifluoromethyl-ethyl)-phenoxy]-ethoxy}-phenyl)-acetamide In analogy to examples 25, 82 and 13.2, from rac [3-(1-phenyl-2-{3-[2,2,2-trifluoro-1-(4-methoxy-benzyloxy)-1-trifluoromethyl-ethyl]-phenoxy}-ethoxy)-phenyl]-acetic acid (example 91) and dimethylamine HCl was prepared rac N,N-dimethyl-2-(3-{1-phenyl-2-[3-(2,2,2-trifluoro-1-hydroxy-1-trifluoromethyl-ethyl)-phenoxy]-ethoxy}-phenyl)-acetamide as an off-white powder, MS: 542 (M+H)+.

Example 91

2-(4-{2-[3-(4-Bromo-phenyl)-benzo[d]isothiazol-6-yloxy]-ethoxy}-phenyl)-1,1,1,3,3,3-hexafluoro-propan-2-ol 95.1

In analogy to example 8.1, from 3-(4-bromo-phenyl)-benzo[d]isothiazol-6-ol (CAS 192443-17-7, prepared according to EP778271) and 2-bromo-ethanol was prepared 2-[3-(4-bromo-phenyl)-benzo[d]isothiazol-6-yloxy]-ethanol as a light yellow solid, MS: 350 (M+H, 1Br)+.

95.2

In analogy to examples 8.2 and 29.3, from 4-[2,2,2-trifluoro-1-(4-methoxy-benzyloxy)-1-trifluoromethyl-ethyl]-phenol (example 1) and 2-[3-(4-bromo-phenyl)-benzo[d]isothiazol-6-yloxy]-ethanol was prepared 2-(4-{2-[3-(4-bromo-phenyl)-benzo[d]isothiazol-6-yloxy]-ethoxy}-phenyl)-1,1,1,3,3,3-hexafluoro-propan-2-ol as a white solid, MS: 590 (M−H, 1Br)−.

Example 92

1,1,1,3,3,3-Hexafluoro-2-{4-[3-(7-propyl-3-trifluoromethyl-benzo[d]isoxazol-6-yloxy)-propoxy]-phenyl}-propan-2-ol In analogy to examples 8.1 and 8.3, from 4-[2,2,2-trifluoro-1-(4-methoxy-benzyloxy)-1-trifluoromethyl-ethyl]-phenol (example 1) and 6-(3-bromo-propoxy)-7-propyl-3-trifluoromethyl-benzo[d]isoxazole (CAS 194608-95-2, prepared according to WO9728137) was prepared 1,1,1,3,3,3-hexafluoro-2-{4-[3-(7-propyl-3-trifluoromethyl-benzo[d]isoxazol-6-yloxy)-propoxy]-phenyl}-propan-2-ol as a colorless oil, MS: 544 (M−H)−.

Example 93

1,1,1,3,3,3-Hexafluoro-2-{3-[3-(7-propyl-3-trifluoromethyl-benzo[d]isoxazol-6-yloxy)-propoxy]-phenyl}-propan-2-ol In analogy to examples 8.1 and 8.3, from 3-[2,2,2-trifluoro-1-(4-methoxy-benzyloxy)-1-trifluoromethyl-ethyl]-phenol (example 5) and 6-(3-bromo-propoxy)-7-propyl-3-trifluoromethyl-benzo[d]isoxazole (CAS 194608-95-2, prepared according to WO9728137) was prepared 1,1,1,3,3,3-hexafluoro-2-{3-[3-(7-propyl-3-trifluoromethyl-benzo[d]isoxazol-6-yloxy)-propoxy]-phenyl}-propan-2-ol as a colorless oil, MS: 544 (M−H)−.

Example 94

(4-{3-[3-(2,2,2-Trifluoro-1-hydroxy-1-trifluoromethyl-ethyl)-phenoxy]-propoxy}-phenyl)-acetic acid methyl ester In analogy to examples 8.1 and 30.4, from 3-[2,2,2-trifluoro-1-(4-methoxy-benzyloxy)-1-trifluoromethyl-ethyl]-phenol (example 5) and [4-(3-bromo-propoxy)-phenyl]-acetic acid methyl ester (CAS 203071-48-1) was prepared (4-{3-[3-(2,2,2-trifluoro-1-hydroxy-1-trifluoromethyl-ethyl)- phenoxy]-propoxy}-phenyl)-acetic acid methyl ester as a colorless oil, MS: 465 (M–H)⁻.

Example 95

(3-{3-[3-(2,2,2-Trifluoro-1-hydroxy-1-trifluoromethyl-ethyl)-phenoxy]-propoxy}-phenyl)-acetic acid methyl ester 95.1
In analogy to example 8.1, from 3-[2,2,2-trifluoro-1-(4-methoxy-benzyloxy)-1-trifluoromethyl-ethyl]-phenol (example 5) and 3-bromo-1-propanol was prepared 3-{3-[2,2,2-trifluoro-1-(4-methoxy-benzyloxy)-1-trifluoromethyl-ethyl]-phenoxy}-propan-1-ol as a colorless liquid, MS: 438 (M)⁺.

95.2
In analogy to examples 8.2 and 30.4, from 3-{3-[2,2,2-trifluoro-1-(4-methoxy-benzyloxy)-1-trifluoromethyl-ethyl]-phenoxy}-propan-1-ol and (3-hydroxy-phenyl)-acetic acid methyl ester was prepared (3-{3-[3-(2,2,2-trifluoro-1-hydroxy-1-trifluoromethyl-ethyl)-phenoxy]-propoxy}-phenyl)-acetic acid methyl ester as a colorless oil, MS: 465 (M–H)⁻.

Example 96

3-(4-{3-[3-(2,2,2-Trifluoro-1-hydroxy-1-trifluoromethyl-ethyl)-phenoxy]-propoxy}-phenyl)-propionic acid methyl ester In analogy to examples 8.2 and 30.4, from 3-{3-[2,2,2-trifluoro-1-(4-methoxy-benzyloxy)-1-trifluoromethyl-ethyl]-phenoxy}-propan-1-ol and 3-(4-hydroxy-phenyl)-propionic acid methyl ester was prepared 3-(4-{3-[3-(2,2,2-trifluoro-1-hydroxy-1-trifluoromethyl-ethyl)-phenoxy]-propoxy}-phenyl)-propionic acid methyl ester as a colorless oil, MS: 479 (M–H)⁻.

Example 97

3-(4-{3-[3-(2,2,2-Trifluoro-1-hydroxy-1-trifluoromethyl-ethyl)-phenoxy]-propoxy}-phenyl)-propionic acid In analogy to example 25, from 3-(4-{3-[3-(2,2,2-trifluoro-1-hydroxy-1-trifluoromethyl-ethyl)-phenoxy]-propoxy}-phenyl)-propionic acid methyl ester (example 96) was prepared 3-(4-{3-[3-(2,2,2-trifluoro-1-hydroxy-1-trifluoromethyl-ethyl)-phenoxy]-propoxy}-phenyl)-propionic acid as a colorless oil, MS: 465 (M–H)⁻.

Example 98

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesium stearate and compressed to yield kernels of 120 or 350 mg respectively. The kernels are lacquered with an aqueous solution/suspension of the above mentioned film coat.

Example 99

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 100

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 101

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |

-continued

| | |
|---|---|
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 102

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Example 103

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce glutathione-s-transferase (GST) fused to the ligand binding domains (LBD) of human LXR alpha (aa 164 to 447) and human LXR beta (aa 155 to 460). To accomplish this, the portions of the sequences encoding the LBDs were amplified from full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of GST-LBD fusion proteins were performed in E. coli strain BL21(pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of GST-LXR alpha-LBD or 700 ng of GST-LXR beta-LBD fusion proteins were bound to 80 µg or 40 µg SPA beads (Pharmacia Amersham) respectively, in a final volume of 50 µl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 µl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plates at a density of $10^5$ Cells/well and then batch-transfected with either the full-length-LXR alpha or full-length-LXR beta expression plasmids plus a reporter plasmid expressing luceriferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 µl of phenol red-free medium containing the test substances or control ligands (final DMSO concentration: 0.1%). Following incubation of the cells for 24 hours with substances, 50 µl of the supernatant was discarded and then 50 µl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 1 nM to 100 µM, preferably 1 nM to 10 µM, more preferably 1 nM to 1 µM.

For example, the following compounds showed the following IC50 values in the binding assay:

| Example | LXRalpha Binding IC50 [µmol/l] | LXRbeta Binding IC50 [µmol/l] |
|---|---|---|
| 11 | 0.093 | 0.014 |
| 13 | 0.237 | 0.236 |
| 57 | 0.033 | 0.0227 |

These results have been obtained by using the foregoing test.

It is to be understood that the invention is not limited to the particular embodiments of the invention described above, as variations of the particular embodiments may be made and still fall within the scope of the appended claims.

What is claimed is:

1. A compound of the formula (I):

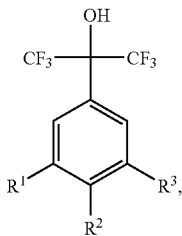

wherein:
R$^1$ is hydrogen, lower-alkyl, or halogen;
one of R$^2$ and R$^3$ is hydrogen, lower-alkyl, or halogen; and the other of R$^2$ and R$^3$ is —O—CHR$^4$—(CH$_2$)$_m$—(CHR$^5$)$_n$—R$^6$;
R$^4$ is hydrogen, lower-alkyl, aryl, aryl-lower-alkyl, heteroaryl, or heteroaryl-lower-alkyl;
R$^5$ is hydrogen or aryl;
R$^6$ is phenyl or aryl-lower-alkyl, which phenyl or aryl-lower-alkyl is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is 5- to 6-membered monocyclic heteroaryl which is optionally substituted with 1 to 3 substituents selected from the group consisting of lower-alkyl, fluoro-lower-alkyl, halogen and aryl, which aryl is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is 9-membered bicyclic heteroaryl which is optionally substituted with 1 to 3 substituents selected from the group consisting of lower-alkyl, fluoro-lower-alkyl, halogen and aryl, which aryl is optionally substituted with 1 to 3 substituents consisting of, amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^6$ is heteroaryl-lower-alkyl which is optionally substituted with 1 to 3 substituents selected from the group consisting of lower-alkyl, fluoro-lower-alkyl, halogen and aryl, which aryl is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl R$^{12}$R$^{13}$NC(O)-lower-alkyl, lower-alkoxy and aryl-lower-alkoxy;
or R$^6$ is —O—R$^7$ or lower-alkyl-OR$^7$;
R$^7$ is aryl which is optionally substituted with 1 to 3 substituents selected from the group consisting of amino, halogen, lower-alkyl, fluoro-lower-alkyl, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy and aryl-lower-alkoxy;
or R$^7$ is heteroaryl which is optionally substituted with 1 to 3 substituents selected from the group consisting of lower-alkyl, fluoro-lower-alkyl, halogen, amino, hydroxy-lower-alkyl, R$^8$—O—C(O)—, R$^9$R$^{10}$NC(O)—, R$^{11}$—O—C(O)-lower-alkyl, R$^{12}$R$^{13}$NC(O)-lower-alkyl, lower-alkoxy, aryl-lower-alkoxy and aryl, which aryl is optionally substituted with 1 to 3 substituents selected from the group consisting of lower-alkyl and halogen;
R$^8$, R$^9$, R$^{10}$, R$^{11}$, R$^{12}$ and R$^{13}$ independently from each other are hydrogen or lower-alkyl;
m is 0 to 3;
n is 0 or 1;
and pharmaceutically acceptable salts and esters thereof.

2. The compound according to claim 1, wherein R$^1$ is hydrogen, chlorine or methyl.

3. The compound according to claim 1, wherein one of R$^2$ and R$^3$ is hydrogen or lower-alkyl, and the other of R$^2$ and R$^3$ is —O—CHR$^4$—(CH$_2$)$_m$—(CHR$^5$)$_n$—R$^6$, wherein R$^4$, R$^5$, R$^6$, m and n are as defined in claim 1.

4. The compound according to claim 1, wherein R$^2$ is —O—CHR$^4$—(CH$_2$)$_m$—(CHR$^5$)$_n$—R$^6$, and R$^3$ is hydrogen, wherein R$^4$, R$^5$, R$^6$, m and n are as defined in claim 1.

5. The compound according to claim 1, wherein R$^4$ is hydrogen, lower-alkyl, aryl, or aryl-lower-alkyl.

6. The compound according to claim 1, wherein R$^4$ is hydrogen, lower-alkyl, or aryl-lower-alkyl.

7. The compound according to claim 1, wherein R$^4$ is hydrogen, methyl or benzyl.

8. The compound according to claim 1, wherein n is 1 and R$^5$ is aryl.

9. The compound according to claim 1, wherein n is 1 and R$^5$ is phenyl.

10. The compound according to claim 1, wherein R$^6$ is phenyl which is optionally substituted with R$^8$—O—C(O)—, or R$^6$ is 5- to 6-membered monocyclic heteroaryl which is optionally substituted with 1 to 3 substituents selected from the group consisting of lower-alkyl and aryl, which aryl is optionally substituted with 1 to 3 substituents selected from the group consisting of halogen, lower-alkyl, fluoro-lower-alkyl, hydroxy-lower-alkyl, R$^8$—O—C(O)— and R$^9$R$^{10}$NC(O)—, wherein R$^8$, R$^9$ and R$^{10}$ are as defined in claim 1.

11. The compound according to claim 1, wherein R$^6$ is phenyl, or R$^6$ is oxazolyl, which oxazolyl is substituted with lower-alkyl and phenyl, which phenyl is substituted with halogen, fluoro-lower-alkyl or hydroxy-lower-alkyl.

12. The compound according to claim 1, wherein R$^6$ is phenyl, 2-(3-chloro-phenyl)-5- methyl-oxazol-4-yl, 5-methyl-2-(3-trifluoromethyl-phenyl)-oxazol-4-yl, or 2-(3-hydroxymethyl-phenyl)-5-methyl-oxazol-4-yl.

13. The compound according to claim 1, wherein R$^6$ is —O—R$^7$, wherein R$^7$ is phenyl which is substituted with 1 substituent selected from the group consisting of hydroxy-lower-alkyl, R$^{11}$—O—C(O)-lower-alkyl and R$^{12}$R$^{13}$NC(O)-lower-alkyl, or R$^7$ is heteroaryl selected from the group consisting of benzo[d] isothiazolyl and benzo[d]isoxazolyl, which heteroaryl is optionally substituted with 1 to 2 substituents selected from the group consisting of lower-alkyl, fluoro-lower-alkyl and phenyl, which phenyl is optionally substituted with halogen, wherein R$^{11}$, R$^{12}$ and R$^{13}$ are as defined in claim 1.

14. The compound according to claim 13, wherein R$^7$ is phenyl substituted with lower-alkoxy-carbonyl or lower-alkoxy-carbonyl-lower-alkyl.

15. The compound according to claim 14, wherein R$^7$ is 3-methoxycarbonylmethyl-phenyl, 4-methoxycarbonylmethyl-phenyl, or 4-methoxycarbonyl-phenyl.

16. The compound according to claim 1, wherein m is 0 to 2.

17. The compound according to claim 1, wherein m is 0 or 1.

18. The compound according to claim 1, wherein n is 0.

19. The compound according to claim 1, selected from the group consisting of 2-(4-{3-[3-(4-Bromo-phenyl)-benzo[d]isothiazol-6-yloxy]-propoxy}-phenyl)-1,1,1,3,3,3-hexafluoro-propan-2-ol, 3-(3-{3-[3-(2,2,2-Trifluoro-1-hydroxy-1-trifluoromethyl-ethyl)-phenoxy]-propoxy}-phenyl)-propionic acid ethyl ester, rac (4-{1-Phenyl-2-[3-(2,2,2-trifluoro-1-hydroxy-1-trifluoromethyl-ethyl)-phenoxy]-ethoxy}-phenyl)-acetic acid methyl ester, rac (4-{1-Phenyl-2-[3-(2,2,2-trifluoro-1-hydroxy-1-trifluoromethyl-ethyl)-phenoxy]-ethoxy}-phenyl)-acetic acid, rac 4-{1-Phenyl-2-[4-(2,2,2-trifluoro-1-hydroxy-1-trifluoromethyl-ethyl)-phenoxy]-ethoxy}-benzoic acid methyl ester, 4-{2-[4-(2,2,2-Trifluoro-1-hydroxy-1-trifluoromethyl-ethyl)-phenoxy]-ethoxy}-benzoic acid methyl ester, 2-(4-Benzyloxy-3-chloro-phenyl)-1,1,1,3,3,3-hexafluoro-propan-2-ol, 2-(4-Benzyloxy-3-methyl-phenyl)-1,1,1,3,3,3-hexafluoro-propan-2-ol, 2-(3-Benzyloxy-phenyl)-1,1,1,3,3,3-hexafluoro-propan-2-ol, 2-(4-Benzyloxy-3,5-dimethyl-phenyl)-1,1,1,3,3,3-hexafluoro-propan-2-ol, 2-(4-Benzyloxy-phenyl)-1,1,1,3,3,3-hexafluoro-propan-2-ol, (4-{3-[2-Methyl-4-(2,2,2-trifluoro-1-hydroxy-1-trifluoromethyl-ethyl)-phenoxy]-propoxy}-phenyl)-acetic acid methyl ester, 4-{3-[2-Methyl-4-(2,2,2-trifluoro-1-hydroxy-1-trifluoromethyl-ethyl)-phenoxy]-propoxy}-benzoic acid methyl ester, 3-(4-{3-[2-Chloro-4-(2,2,2-trifluoro-1-hydroxy-1-trifluoromethyl-ethyl)-phenoxy]-propoxy}-phenyl)-propionic acid methyl ester, (4-{3-[2-Chloro-4-(2,2,2-trifluoro-1-hydroxy-1-trifluoromethyl-ethyl)-phenoxy]-propoxy}-phenyl)-acetic acid methyl ester, 4-{3-[2-Chloro-4-(2,2,2-trifluoro-1-hydroxy-1-trifluoromethyl-ethyl)-phenoxy]-propoxy}-benzoic acid methyl ester, (4-{3-[2,6-Dimethyl-4-(2,2,2-trifluoro-1-hydroxy-1-trifluoromethyl-ethyl)-phenoxy]-propoxy}-phenyl)-acetic acid methyl ester, 4-{3-[2,6-Dimethyl-4-(2,2,2-trifluoro-1-hydroxy-1-trifluoromethyl-ethyl)-phenoxy]-propoxy}-benzoic acid methyl ester, 4-{3-[2-Methyl-4-(2,2,2-trifluoro-1-hydroxy-1-trifluoromethyl-ethyl)-phenoxy]-propoxy}-benzoic acid, (4-{3-[2-Methyl-4-(2,2,2-trifluoro-1-hydroxy-1-trifluoromethyl-ethyl)-phenoxy]-propoxy}-phenyl)-acetic acid, (4-{3-[2,6-Dimethyl-4-(2,2,2-trifluoro-1-hydroxy-1-trifluoromethyl-ethyl)-phenoxy]-propoxy}-phenyl)-acetic acid, 4-{3-[2,6-Dimethyl-4-(2,2,2-trifluoro-1-hydroxy-1-trifluoromethyl-ethyl)-phenoxy]-propoxy}-benzoic acid, 4-{2-[2,6-Dimethyl-4-(2,2,2-trifluoro-1-hydroxy-1-trifluoromethyl-ethyl)-phenoxy]-ethoxy}-benzoic acid methyl ester, 3-(4-{(S)-2-[2-Methyl-4-(2,2,2-trifluoro-1-hydroxy-1-trifluoromethyl-ethyl)-phenoxy]-3-phenyl-propoxy}-phenyl)-propionic acid methyl ester, (4-{(S)-2-[2-Methyl-4-(2,2,2-trifluoro-1-hydroxy-1-trifluoromethyl-ethyl)-phenoxy]-3-phenyl-propoxy}-phenyl)-acetic acid methyl ester, 4-{(S)-2-[2-Methyl-4-(2,2,2-trifluoro-1-hydroxy-1-trifluoromethyl-ethyl)-phenoxy]-3-phenyl-propoxy}-benzoic acid methyl ester, (4-{(S)-3-Phenyl-2-[4-(2,2,2-trifluoro-1-hydroxy-1-trifluoromethyl-ethyl)-phenoxy]-propoxy}-phenyl)-acetic acid methyl ester, 4-{(S)-3-Phenyl-2-[4-(2,2,2-trifluoro-1-hydroxy-1-trifluoromethyl-ethyl)-phenoxy]-propoxy}-benzoic acid methyl ester, (4-{(S)-2-[2-Methyl-4-(2,2,2-trifluoro-1-hydroxy-1-trifluoromethyl-ethyl)-phenoxy]-3-phenyl-propoxy}-phenyl)-acetic acid, 4-{(S)-2-[2-Methyl-4-(2,2,2-trifluoro-1-hydroxy-1-trifluoromethyl-ethyl)-phenoxy]-3-phenyl-propoxy}-benzoic acid, (4-{(S)-3-Phenyl-2-[4-(2,2,2-trifluoro-1-hydroxy-1-trifluoromethyl-ethyl)-phenoxy]-propoxy}-phenyl)-acetic acid, 4-{(S)-3-Phenyl-2-[4-(2,2,2-trifluoro-1-hydroxy-1-trifluoromethyl-ethyl)-phenoxy]-propoxy}-benzoic acid, rac 1,1,1,3,3,3-Hexafluoro-2-{4-[2-(4-hydroxymethyl-phenoxy)-1-phenyl-ethoxy]-phenyl}-propan-2-ol, 1,1,1,3,3,3-Hexafluoro-2-(3-methyl-4-phenethyloxy-phenyl)-propan-2-ol, rac 1,1,1,3,3,3-Hexafluoro-2-[3-methyl-4-(1-phenyl-ethoxy)-phenyl]-propan-2-ol, 2-{4-[2-(3-Chloro-phenyl)-5-methyl-oxazol-4-yl-methoxy]-phenyl}-1,1,1,3,3,3-hexafluoro-propan-2-ol, 2-[4-(3,5-Dimethyl-isoxazol-4-ylmethoxy)-phenyl]-1,1,1,3,3, 3-hexafluoro-propan-2-ol, 1,1,1,3,3,3-Hexafluoro-2-[4-(5-methyl-isoxazol-3-yl-methoxy)-phenyl]-propan-2-ol, 1,1,1,3,3,3-Hexafluoro-2-[4-(5-methyl-2-phenyl-2#H!-[1,2,3]triazol-4-ylmethoxy)-phenyl]-propan-2-ol, 1,1,1,3,3,3-Hexafluoro-2-[4-(5-methyl-3-phenyl-isoxazol-4-ylmethoxy)-phenyl]-propan-2-ol, 3-[4-(2,2,2-Trifluoro-1-hydroxy-1-trifluoromethyl-ethyl)-phenoxymethyl]-benzoic acid methyl ester, 4-{(S)-2-[2-methyl-4-(2,2,2-trifluoro-1-hydroxy-1-trifluoromethyl-ethyl)-phenoxy]-3-phenyl-propoxy}-benzoic acid, (4-{(S)-3-phenyl-2-[4-(2,2,2-trifluoro-1-hydroxy-1-trifluoromethyl-ethyl)-phenoxy]-propoxy}-phenyl)-acetic acid, 3-(4-{(R)-3-Phenyl-2-[4-(2,2,2-trifluoro-1-hydroxy-1-trifluoromethyl-ethyl)-phenoxy]-propoxy}-phenyl)-propionic acid methyl ester, (4-{(R)-3-Phenyl-2-[4-(2,2,2-trifluoro-1-hydroxy-1-trifluoromethyl-ethyl)-phenoxy]-propoxy}-phenyl)-acetic acid methyl ester, 4-{(R)-3-Phenyl-2-[4-(2,2,2-trifluoro-1-hydroxy-1-trifluoromethyl-ethyl)-phenoxy]-propoxy}-benzoic acid methyl ester, 3-(4-{(R)-3-Phenyl-2-[4-(2,2,2-trifluoro-1-hydroxy-1-trifluoromethyl-ethyl)-phenoxy]-propoxy}-phenyl)-propionic acid, (4-{(R)-3-Phenyl-2-[4-(2,2,2-trifluoro-1-hydroxy-1-trifluoromethyl-ethyl)-phenoxy]-propoxy}-phenyl)-acetic acid, 4-{(R)-3-Phenyl-2-[4-(2,2,2-trifluoro-1-hydroxy-1-trifluoromethyl-ethyl)-phenoxy]-propoxy}-benzoic acid, 2-{4-[2-(3-Chloro-phenyl)-5-methyl-oxazol-4-yl-methoxy]-3-methyl-phenyl}-1,1,1,3,3,3-hexafluoro-propan-2-ol, 2-{3-Chloro-4-[2-(3-chloro-phenyl)-5-methyl-oxazol-4-ylmethoxy]-phenyl}-1,1,1,3,3,3-hexafluoro-propan-2-ol, 1,1,1,3,3,3-Hexafluoro-2-(4-phenethyloxy-phenyl)-propan-2-ol, 2-(3,5-Dimethyl-4-phenethyloxy-phenyl)-1,1,1,3,3,3-hexafluoro-propan-2-ol, 2-(3-Chloro-4-phenethyloxy-phenyl)-1,1,1,3,3,3-hexafluoro-propan-2-ol, rac 1,1,1,3,3,3-Hexafluoro-2-[4-(1-phenyl-ethoxy)-phenyl]-propan-2-ol, 1,1,1,3,3,3-Hexafluoro-2-[3-methyl-4-(5-methyl-2-m-tolyl-oxazol-4-ylmethoxy)-phenyl]-propan-2-ol, 2-{4-[2-(2-Chloro-phenyl)-5-methyl-oxazol-4-yl-methoxy]-3-methyl-phenyl}-1,1,1,3,3,3-hexafluoro-propan-2-ol, 1,1,1,3,3,3-Hexafluoro-2-[3-methyl-4-(5-methyl-2-o-tolyl-oxazol-4-ylmethoxy)-phenyl]-propan-2-ol, 1,1,1,3,3,3-Hexafluoro-2-{3-methyl-4-[5-methyl-2-(3-trifluoromethyl-phenyl)-oxazol-4-ylmethoxy]-phenyl}-propan-2-ol, 1,1,1,3,3,3-Hexafluoro-2-{4-[2-(4-fluoro-3-methyl-phenyl)-5-methyl-oxazol-4-ylmethoxy]-3-methyl-phenyl}-propan-2-ol, 2-{3-Chloro-4-[5-methyl-2-(4-trifluoromethyl-phenyl)-oxazol-4-ylmethoxy]-phenyl}-1,1,1,3,3,3-hexafluoro-propan-2-ol, 2-[3-Chloro-4-(5-methyl-2-m-tolyl-oxazol-4-yl-methoxy)-phenyl]-1,1,1,3,3,3-hexafluoro-propan-2-ol, 2-{3-Chloro-4-[2-(2-chloro-phenyl)-5-methyl-oxazol-4-ylmethoxy]-phenyl}-1,1,1,3,3,3-hexafluoro-propan-2-ol, 2-[3-Chloro-4-(5-methyl-2-o-tolyl-oxazol-4-ylmethoxy)-phenyl]-1,1,1,3,3,3-hexafluoro-propan-2-ol, 2-{3-Chloro-4-[5-methyl-2-(3-trifluoromethyl-phenyl)-oxazol-4-ylmethoxy]-phenyl}-1,1,1,3,3,3-hexafluoro-propan-2-ol, 2-{3-Chloro-4-[2-(4-fluoro-3-methyl-phenyl)-5-methyl-oxazol-4-ylmethoxy]-phenyl}-1,1,1,3,3,3-hexafluoro-propan-2-ol, 2-{3-[2-(3-Chloro-phenyl)-5-methyl-oxazol-4-yl-methoxy]-phenyl}-1,1,1,3,3,3-hexafluoro-propan-2-ol, 1,1,1,3,3,3-Hexafluoro-2-[3-(5-methyl-2-o-tolyl-oxazol-4-ylmethoxy)-phenyl]-propan-2-ol, 1,1,1,3,3,3-Hexafluoro-2-{3-[5-methyl-2-(3-trifluoromethyl-phenyl)-oxazol-4-ylmethoxy]-phenyl}-propan-2-ol, 2-{3-[2-(2-Chloro-phenyl)-5-methyl-oxazol-4-yl-methoxy]-phenyl}-1,1,1,3,3,3-hexafluoro-propan-2-ol, 1,1,1,3,3,3-Hexafluoro-2-[3-(5-methyl-2-m-tolyl-oxazol-4-ylmethoxy)-phenyl]-propan-2-ol, 3-{4-[2-Chloro-4-(2,2,2-trifluoro-1-hydroxy-1-trifluoromethyl-ethyl)-phenoxymethyl]-5-methyl-oxazol-2-yl}-benzoic acid methyl ester, 2-{3-Chloro-4-[2-(3-hydroxymethyl-phenyl)-5-methyl-oxazol-4-ylmethoxy]-phenyl}-1,1,1,3,3,3-hexafluoro-propan-2-ol, 4-{5-Methyl-4-[3-(2,2,2-trifluoro-1-hydroxy-1-trifluoromethyl-ethyl)-phenoxymethyl]-oxazol-2-yl}-benzoic acid methyl ester, 4-{5-Methyl-4-[3-(2,2,2-trifluoro-1-hydroxy-1-trifluoromethyl-ethyl)-phenoxymethyl]-oxazol-2-yl}-benzoic acid, N,N-Dimethyl-4-{5-methyl-4-[3-(2,2,2-trifluoro-1-hydroxy-1-trifluoromethyl-ethyl)-phenoxymethyl]-oxazol-2-yl}-benzamide, (3-{2-[4-(2,2,2-Trifluoro-1-hydroxy-1-trifluoromethyl-ethyl)-phenoxy]-ethoxy}-phenyl)-acetic acid methyl ester, (4-{2-[4-(2,2,2-Trifluoro-1-hydroxy-1-trifluoromethyl-ethyl)-phenoxy]-ethoxy}-phenyl)-acetic acid methyl ester, (3-{2-[3-(2,2,2-Trifluoro-1-hydroxy-1-trifluoromethyl-ethyl)-phenoxy]-ethoxy}-phenyl)-acetic acid methyl ester, (3-{2-[4-(2,2,2-Trifluoro-1-hydroxy-1-trifluoromethyl-ethyl)-phenoxy]-ethoxy}-phenyl)-acetic acid, (4-{2-[4-(2,2,2-Trifluoro-1-hydroxy-1-trifluoromethyl-ethyl)-phenoxy]-ethoxy}-phenyl)-acetic acid, rac (3-{1-Phenyl-2-[3-(2,2,2-trifluoro-1-hydroxy-1-trifluoromethyl-ethyl)-phenoxy]-ethoxy}-phenyl)-acetic acid methyl ester, rac (3-{1-Phenyl-2-[3-(2,2,2-trifluoro-1-hydroxy-1-trifluoromethyl-ethyl)-phenoxy]-ethoxy}-phenyl)-acetic acid, rac N,N-Dimethyl-2-(3-{1-phenyl-2-[3-(2,2,2-trifluoro-1-hydroxy-1-trifluoromethyl-ethyl)-phenoxy]-ethoxy}-phenyl)-acetamide, 2-(4-{2-[3-(4-Bromo-phenyl)-benzo[d]isothiazol-6-yloxy]-ethoxy}-phenyl)-1,1,1,3,3,3-hexafluoro-propan-2-ol, 1,1,1,3,3,3-Hexafluoro-2-{4-[3-(7-propyl-3-trifluoromethyl-benzo[d]isoxazol-6-yloxy)-propoxy]-phenyl}-propan-2-ol, 1,1,1,3,3,3-Hexafluoro-2-{3-[3-(7-propyl-3-trifluoromethyl-benzo[d]isoxazol-6-yloxy)-propoxy]-phenyl}-propan-2-ol, (4-{3-[3-(2,2,2-Trifluoro-1-hydroxy-1-trifluoromethyl-ethyl)-phenoxy]-propoxy}-phenyl)-acetic acid methyl ester, (3-{3-[3-(2,2,2-Trifluoro-1-hydroxy-1-trifluoromethyl-ethyl)-phenoxy]-propoxy}-phenyl)-acetic acid methyl ester, 3-(4-{3-[3-(2,2,2-Trifluoro-1-hydroxy-1-trifluoromethyl-ethyl)-phenoxy]-propoxy}-phenyl)-propionic acid methyl ester, and 3-(4-{3-[3-(2,2,2-Trifluoro-1-hydroxy-1-trifluoromethyl-ethyl)-phenoxy]-propoxy}-phenyl)-propionic acid, and pharmaceutically acceptable salts and esters thereof.

20. The compound according to claim 1, selected from the group consisting of (3-{2-[4-(2,2,2-Trifluoro-1-hydroxy-1-trifluoromethyl-ethyl)-phenoxy]-ethoxy}-phenyl)-acetic acid methyl ester, rac 4-{1-Phenyl-2-[4-(2,2,2-trifluoro-1-hydroxy-1-trifluoromethyl-ethyl)-phenoxy]-ethoxy}-benzoic acid methyl ester, 2-(4-Benzyloxy-3-chloro-phenyl)-1,1,1,3,3,3-hexafluoro-propan-2-ol, (4-{(S)-3-Phenyl-2-[4-(2,2,2-trifluoro-1-hydroxy-1-trifluoromethyl-ethyl)-phenoxy]-propoxy}-phenyl)-acetic acid methyl ester, 1,1,1,3,3,3-Hexafluoro-2-(3-methyl-4-phenethyloxy-phenyl)-propan-2-ol, rac 1,1,1,3,3,3-Hexafluoro-2-[3-methyl-4-(1-phenyl-ethoxy)-phenyl]-propan-2-ol, 2-{4-[2-(3-Chloro-phenyl)-5-methyl-oxazol-4-yl-methoxy]-phenyl}-1,1,1,3,3,3-hexafluoro-propan-2-ol, (4-{(R)-3-Phenyl-2-[4-(2,2,2-trifluoro-1-hydroxy-1-trifluoromethyl-ethyl)-phenoxy]-propoxy}-phenyl)-acetic acid methyl ester, 2-{3-Chloro-4-[2-(3-chloro-phenyl)-5-methyl-oxazol-4-ylmethoxy]-phenyl}-1,1,1,3,3,3-hexafluoro-propan-2-ol, 2-(3-Chloro-4-phenethyloxy-phenyl)-1,1,1,3,3,3-hexafluoro-propan-2-ol, 1,1,1,3,3,3-Hexafluoro-2-{3-methyl-4-[5-methyl-2-(3-trifluoromethyl-phenyl)-oxazol-4-ylmethoxy]-phenyl}-propan-2-ol, 2-{3-Chloro-4-[5-methyl-2-(3-trifluoromethyl-phenyl)-oxazol-4-yl methoxy]-phenyl}-1,1,1,3,3,3-hexafluoro-propan-2-ol, and 2-{3-Chloro-4-[2-(3-hydroxymethyl-phenyl)-5-methyl-oxazol-4-yl methoxy]-phenyl}-1,1,1,3,3,3-hexafluoro-propan-2-ol, and pharmaceutically acceptable salts and esters thereof.

21. A process for the manufacture of a compound according to claim 1, comprising the steps of:

a) reacting a compound of formula (II)

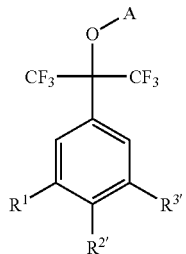

(II)

with a compound HO—CHR$^4$—(CH$_2$)$_m$—(CHR$^5$)$_n$—R$^6$, wherein R$^1$, R$^4$, R$^5$, R$^6$, m and n are as defined in any of claims 1-20, one of R$^{2'}$ and R$^{3'}$ is OH and the other of R$^{2'}$ and R$^{3'}$ is hydrogen, lower-alkyl, or halogen, and A is hydrogen or a protecting group, or b) reacting a compound of formula (II)

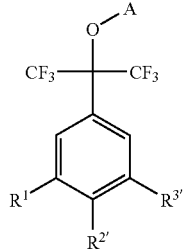

(II)

with a compound LG-CHR$^4$—(CH2)$_m$—(CHR$^5$)$_n$—R$^6$ wherein R$^1$, R$^4$, R$^5$, R$^6$, m and n are as defined in any of claims 1-20, one of R$^{2'}$ and R$^{3'}$ is OH and the other of R$^{2'}$ and R$^{3'}$ is hydrogen, lower-alkyl, or halogen, LG is a leaving group and A is hydrogen or a protecting group.

22. A pharmaceutical composition, comprising a compound according to claim 1 and a pharmaceutically acceptable carrier and/or adjuvant.

\* \* \* \* \*